(12) United States Patent
Botvinick et al.

(10) Patent No.: US 8,844,369 B2
(45) Date of Patent: Sep. 30, 2014

(54) CONCENTRATION INDEPENDENT MODULATION OF LOCAL MICROMECHANICS IN A FIBRIN GEL

(75) Inventors: Elliot Botvinick, Irvine, CA (US); Samir Shreim, Irvine, CA (US); Maxwell Kotlarchyk, Costa Mesa, CA (US)

(73) Assignee: The Regents of The University of California, Oakland, CA (US)

( * ) Notice: Subject to any disclaimer, the term of this patent is extended or adjusted under 35 U.S.C. 154(b) by 205 days.

(21) Appl. No.: 13/457,342

(22) Filed: Apr. 26, 2012

(65) Prior Publication Data

US 2012/0272745 A1 Nov. 1, 2012

Related U.S. Application Data

(60) Provisional application No. 61/480,287, filed on Apr. 28, 2011.

(51) Int. Cl.
*G01N 3/24* (2006.01)
*C12M 1/42* (2006.01)
*A61L 27/36* (2006.01)
*G01N 11/14* (2006.01)

(52) U.S. Cl.
CPC ............... *G01N 3/24* (2013.01); *C12M 35/04* (2013.01); *A61L 27/3691* (2013.01); *G01N 11/14* (2013.01); *G01N 2203/0089* (2013.01)
USPC ......................................................... 73/843

(58) Field of Classification Search
CPC . G01N 2203/0092; G01N 3/24; G01N 33/48; G01N 33/483; G01N 33/4833; G01N 2203/0089
USPC ............................................................. 73/843
See application file for complete search history.

(56) References Cited

U.S. PATENT DOCUMENTS

| | | | |
|---|---|---|---|
| 5,486,457 A | 1/1996 | Butler et al. | |
| 7,444,855 B2 * | 11/2008 | Cottais et al. | 73/54.39 |
| 2009/0056424 A1 * | 3/2009 | Cohen et al. | 73/54.37 |
| 2011/0091922 A1 | 4/2011 | Krishnan et al. | |
| 2011/0203355 A1 * | 8/2011 | Lindner et al. | 73/73 |

FOREIGN PATENT DOCUMENTS

GB   1121177 A  *  7/1968  ............. G01N 11/16

OTHER PUBLICATIONS

Brau et al., "Passive and active microrheology with optical tweezers," Journal of Optics A: Pure and Applied Optics: 5103-5112, 2007.
Mizuno et al., "Active and Passive Microrheology in Equilibrium and Nonequilibrium Systems. Macromolecules," 2008.
Winer et al, "Non-linear elasticity of extracellular matrices enables contractile cells to communicate local position and orientation," PLoS One 4: e6382, 2009.

(Continued)

*Primary Examiner* — Max Noori
*Assistant Examiner* — Roger Hernandez-Prewit
(74) *Attorney, Agent, or Firm* — Knobbe Martens Olson & Bear LLP

(57) ABSTRACT

An apparatus and method for providing a gradient strain to an extracellular matrix to induce mechanotransduction. The gradient strain can be produced by adhering the extracellular matrix to a post and the walls of a sample holder, and then rotating the post and the sample holder. This strain can result in increased stiffness of the extracellular matrix with very little loss of pore size.

20 Claims, 23 Drawing Sheets

(56) References Cited

OTHER PUBLICATIONS

Choe, et al., Extracellular Matrix Remodeling by Dynamic Strain in a Three-Dimensional Tissue-Engineered Human Airway Wall Model. American Journal of Respiratory Cell and Molecular Biology, vol. 3, pp. 306-313, 2006.

Putnam et al., Microtubule assembly is regulated by externally applied strain in cultured smooth muscle cells. Journal of Cell Science, vol. 111, pp. 3379-3387, 1998.

* cited by examiner

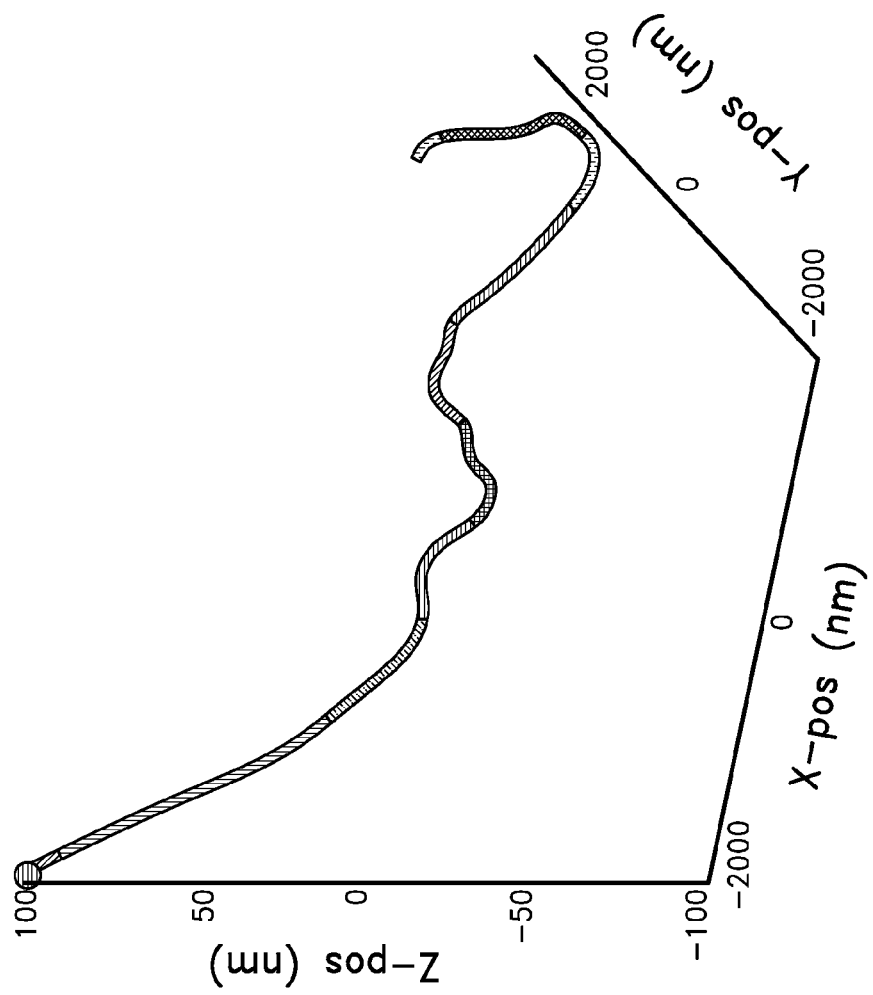
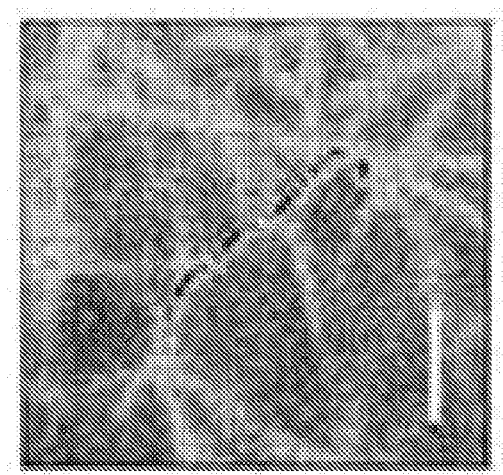
FIG. 21

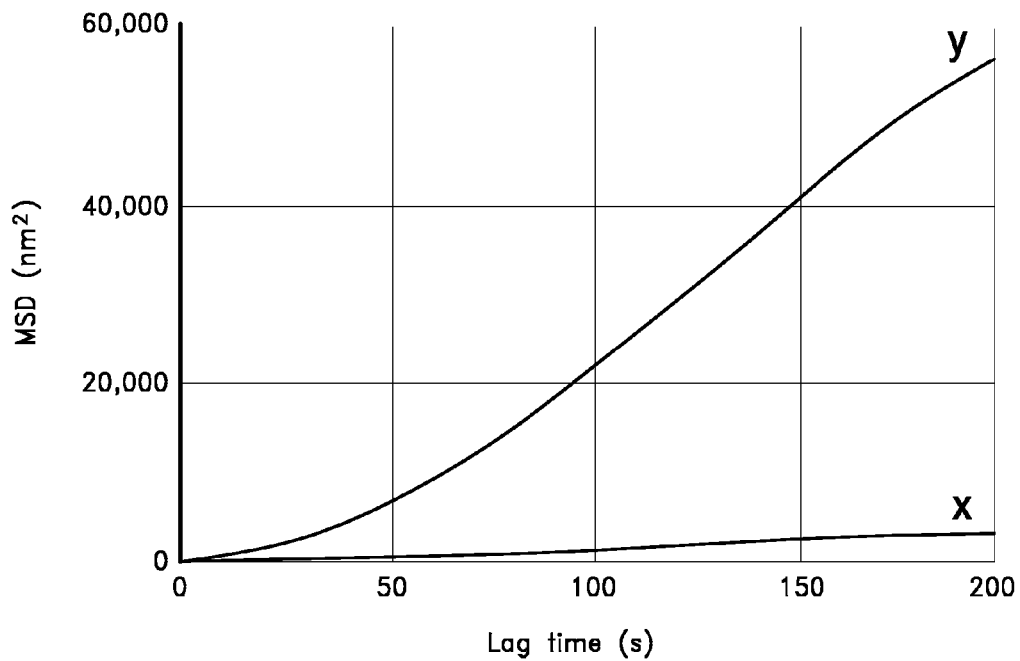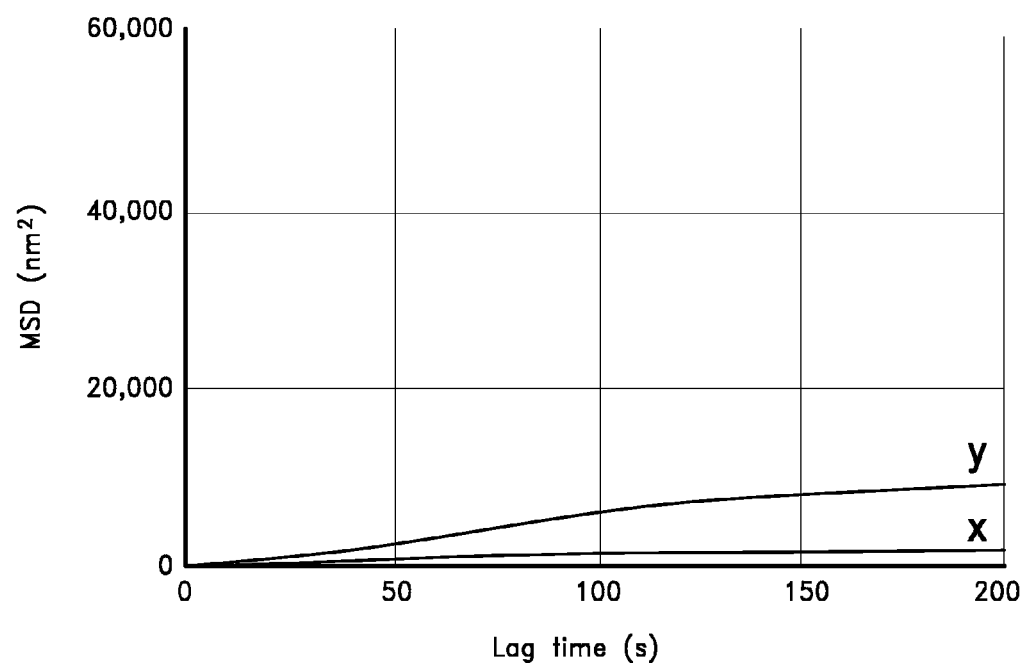
FIG. 23

CONCENTRATION INDEPENDENT MODULATION OF LOCAL MICROMECHANICS IN A FIBRIN GEL

CROSS-REFERENCE TO RELATED APPLICATIONS

This application claims the benefit of priority under 35 U.S.C. §119(e) of U.S. Provisional Application No. 61/480,287 filed on Apr. 28, 2011, incorporated herein by reference in its entirety.

STATEMENT REGARDING FEDERALLY SPONSORED R&D

This invention was made with government support under grants P41-RR001192 and R01-HL085339 awarded by the National Institute of Health and DMR-0805164 funded by the National Science Foundation. The government has certain rights to this invention.

BACKGROUND OF THE INVENTION

1. Field of the Invention

Aspects of the disclosed apparatus and methods relate to providing a gradient strain to an extracellular matrix.

2. Description of the Related Art

Mechanical forces regulate the development and phenotype of a variety of tissues and cultured cells. Previous studies involving mechanotransduction use methods to apply mechanical strain to cells and tissues. These studies suggest that the cell's extracellular matrix (ECM) attachments are the sites at which forces are transmitted to cells. Hydrogels polymerized from natural, synthetic, or hybrid molecules are commonly used as ECM for the study of cell-ECM interactions as well as for medically implantable biomaterials and potential scaffolds for tissue regeneration. The design of a hydrogel that mimics the physiological microenvironment requires consideration of a multitude of factors including micromechanical properties, biocompatibility, ligand concentration, biotransport kinetics, and pore size. Complex interactions between these factors contribute to the transduction of cellular signals, which in turn determines cell survival, proliferation, and phenotype. Uncovering the exact role of stiffness in regulating cells in 3D has proven to be difficult because tuning stiffness in a physiologically relevant system is non-trivial. While the bulk mechanics of 3D matrices can be made effectively more stiff by increasing ECM protein concentration or altering the molecular weight of monomers, there is a resulting decrease in mesh pore size, and increase in cellular confinement, resistance to transport, and local concentration of ligand presented to cells cultured within. Protein-polymer hybrid systems such as PEG-fibrinogen or collagen-agarose allow one to tune stiffness independent from bulk ligand concentration. However, the mesh size of these systems is commonly much smaller than their naturally derived protein hydrogel counterparts, thus increasing both resistance to transport and cellular confinement as compared to naturally derived systems. While phenotypic changes have been demonstrated in such systems, their relevance is debatable in the context of understanding basic physiology.

Fibrin is a commonly used naturally occurring viscoelastic biopolymer. Fibrin is the polymerized form of the blood circulating protein fibrinogen, and is the predominant structural component of blood clots that form in response to injury. Fibrin hydrogels exhibit many interesting mechanical properties, including high extensibility and negative compressibility, all while maintaining permeability and bulk structural integrity under proteolytic degradation and cellular contraction, making it an ideal substrate for the wound healing process. The molecular basis for fibrin's remarkable physical behavior has been investigated at the scale of individual fibers, networks of fibers, and within macro-scale hydrogels. A more complete understanding of the role of fibrin's astounding mechanical properties in disease and thrombosis, as well as its function as a scaffold which drives tissue morphogenesis, will lead to better design strategies for tissue regeneration and engineering.

SUMMARY OF THE INVENTION

In some embodiments, an apparatus for applying strain on an extracellular matrix is disclosed. This apparatus comprises a sample container comprising an ECM, a base configured to securely hold the sample container, a post configured to contact the ECM, and a means for imparting a rotational strain on the ECM. In some embodiments, the means for imparting rotational strain can comprise a ratcheting screw configured to rotate the post relative to the sample container. The some embodiments, the means for imparting rotational strain could also comprise a threaded screw, a spring plunger assembly and a lever arm, configured to rotate the post relative to the sample container. In some embodiments, means for imparting rotational strain comprises a notch on the sample container and a lever configured to rotate the sample container relative to the post. In some embodiments, the means for imparting rotational strain comprises a motor configured to rotate the sample container or the post.

In some embodiments, a force meter is attached to the post or sample container. In some embodiments, the sample container is a petri dish or a cell culture dish. In some embodiments, the rotational strain is non-uniform throughout the ECM. The rotational strain can be applied in both a clockwise and a counterclockwise direction. Also, the apparatus can be configured to connect to a microscope.

In some embodiments, an apparatus for providing a strain gradient to an extracellular matrix is disclosed. The apparatus comprises at least one sample area, an ECM disposed in the sample area, a post configured to contact the ECM, a screw, a spring, and a lever arm with a first end attached to the post and a second end positioned between the screw and the spring.

In some embodiments, a method for applying strain on an extracellular matrix is disclosed. The method comprises providing an ECM within a sample container, contacting a post with the ECM, and rotating at least one of the post or the sample container to create rotational strain on the ECM. In some embodiments, the sample container further comprises cells. In some embodiments, prior to rotating the post or sample container, the ECM is incubated with the post for a time sufficient to promote adhesion of the ECM to the post. In some embodiments the surface area of the post in contact with the ECM is smaller than the surface area of the sample container. In some embodiments, the ECM has a higher stiffness nearer to the post as compared to the ECM farther from the post. In some embodiments the ECM does not increase in stiffness. In some embodiments the ECM has a limited change in pore geometry. In some embodiments, fibers within the ECM have tension applied. In some embodiments the rotating of the post or sample container causes non-uniform strain throughout the ECM. In some embodiments, the post or sample container is rotated in both a clockwise and a counterclockwise direction. In some embodiments, the post and the sample container are rotated.

BRIEF DESCRIPTION OF THE DRAWINGS

FIG. 21 illustrates coiled fibers.

FIG. 23 illustrates mean square displacement (MSD) during post rotation.

DETAILED DESCRIPTION OF THE PREFERRED EMBODIMENT

Figure 1:
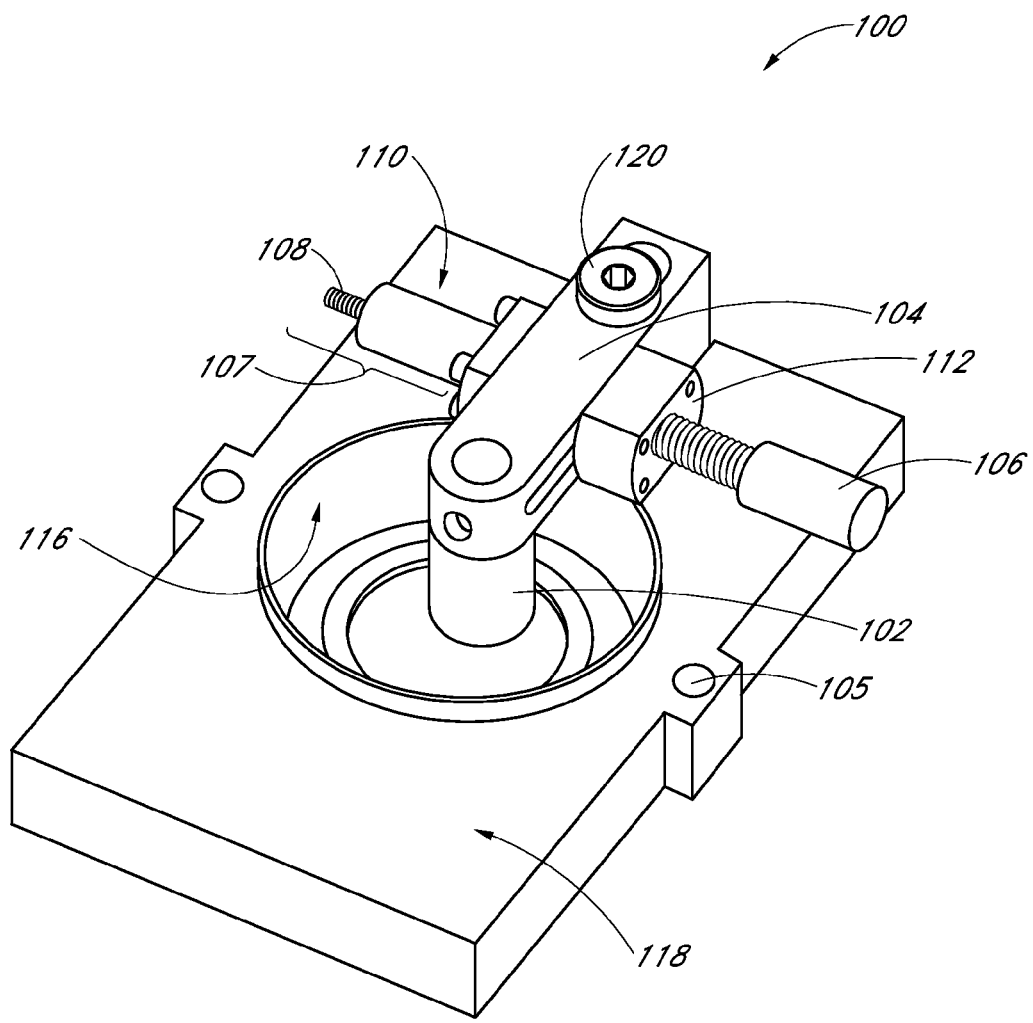
FIG. 1 illustrates an example apparatus for creating stiffness strain-tunable ECMs.

The compositions, materials, methods of preparation, devices, and systems of this disclosure each have several aspects, no single one of which is solely responsible for its desirable attributes. Without limiting the scope of this invention, its more prominent features will now be discussed briefly.

Any terms not directly defined herein shall be understood to have all of the meanings commonly associated with them as understood within the art. Certain terms are discussed below, or elsewhere in the specification, to provide additional guidance to the practitioner in describing the compositions, methods, systems, and the like of various embodiments, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments herein.

An interesting property of naturally derived ECMs, such as fibrin, is their tendency to stiffen with stretch. In fact, most tissues persist in a stretched state. This so called "mechanical homeostasis", where residual stress is present in the absence of any external load, was first demonstrated when excised blood vessels were shown to spring open as they were sliced axially. The residual stress, or prestress, originates from cell contractile forces, which are mediated by actomyosin interactions within cells. Intracellular prestress has been demonstrated by the viscoelastic retraction of photoablated actin stress fibers followed by a decrease in contractility as assessed by traction force microscopy, and by the observation that actin stress fibers within cells cultured on pre-stretched membranes buckle when stretch is released. Cellular traction forces are sufficient to locally deform the ECM, whose stiffness is strain-dependent. Therefore, the stiffness of biological ECMs can be tuned by external mechanical loads alone to study the effects of ECM stiffness on cell physiology in 3D. Apparatuses can be used to induce a strain gradient on an ECM, thereby manipulating the stiffness of the ECM.

The described apparatus enables users to tune the stiffness of naturally derived ECMs, while allowing for continuous optical observation and interrogation. Stiffness can be tuned independent from matrix architecture in a naturally derived matrix such as fibrin. Local gel mechanics can be altered, not through increased protein concentration or exogenous cross-linking, but by directly altering the tensile stress state of the gel's fiber network through the application of shear strain. In contrast to polymer-peptide hybrid systems, the described apparatus allows cell-cell communication of soluble factors through 'natural' pores, where interacting cells may independently experience very different mechanical microenvironments. A strong circumferential gradient in stiffness occurs near to the post as well as at regions far from the post in which the distribution of stiffness was unaltered. Differential stiffening can occur at varying degrees of rotation of the post, thereby allowing tuning of local mechanics by the application of strain. In high strain regions, the original stiffness can be entirely recoverable.

In the context of available photonic technologies such as microrheology, confocal imaging, and multiphoton 3D particle tracking, as well as techniques not yet realized, the described apparatus provides an appropriate platform in which to study cell-ECM interactions while manipulating local mechanics of naturally derived ECMs without altering their composition. The described apparatus can be applied to many ECMs already in use by cell biologists such as those derived from collagen and agarose as well as commercial products such as Matrigel and custom designed protein-polymer hybrids.

Figure 2:
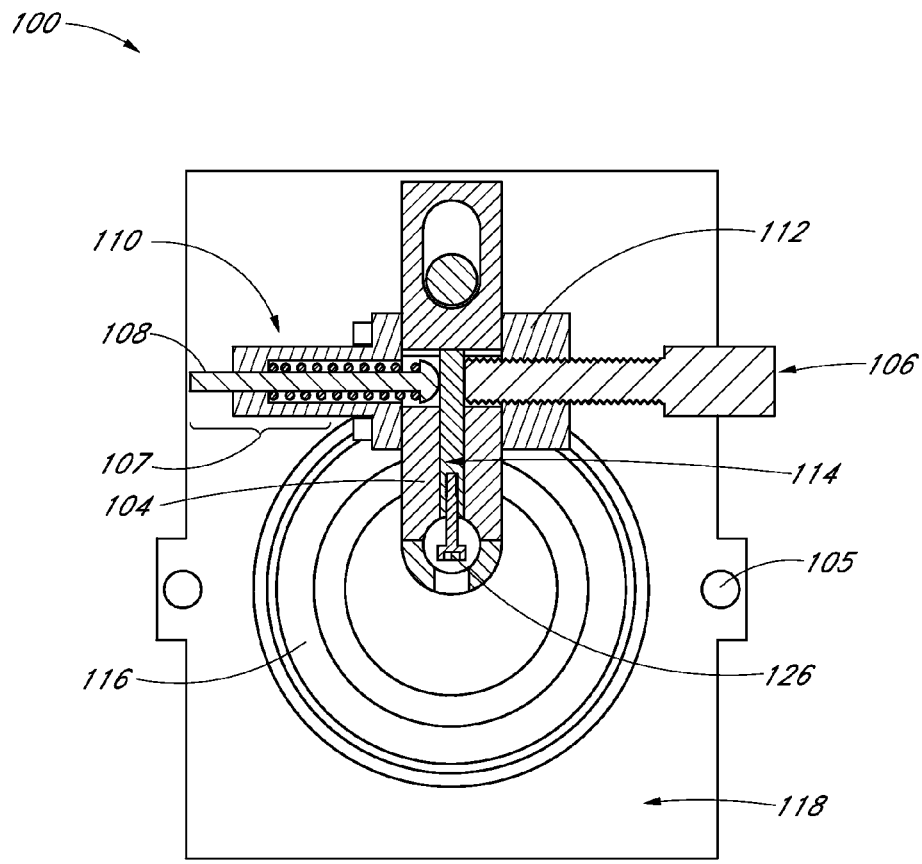
FIG. 2 illustrates a top down view of an example apparatus for creating stiffness strain-tunable ECMs.
Figure 3:
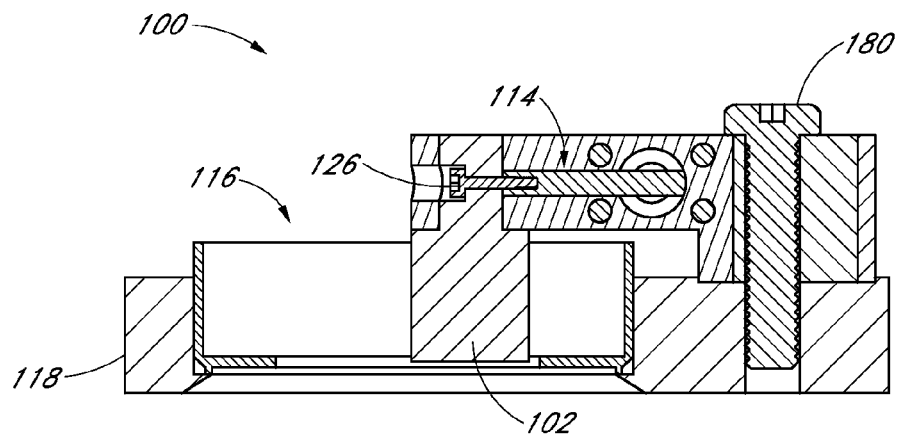
FIG. 3 illustrates a side view of an example apparatus for creating stiffness strain-tunable ECMs.

FIGS. 1-4 illustrate an example apparatus for creating stiffness strain-tunable ECMs. A gradient, or variable, stiffness can be induced by the apparatus by generating a gradient in mechanical strain. FIG. 1 shows a view of an apparatus 100. Referring to FIG. 1, the apparatus 100 contains a post 102. This post 102 is supported by a cantilever arm 104, which connects to a leadscrew 106 and a springer-plunger assembly 107. In some embodiments the leadscrew 106 is attached to a force meter. In some embodiments the leadscrew 106 is attached to a motor. The springer-plunger assembly 107 consists of a spring 108 and a spring holder 110. The leadscrew 106 can be held in place by a lead screw block 112. As the leadscrew 106 is rotated inwards, the lever arm 114 causes a counterclockwise rotation of the post 102. As the leadscrew 106 is rotated out, the spring-plunger assembly 107 pushes the lever arm 114 in the opposite direction, causing clockwise rotation of the post 102. The post 102 can be in contact with the ECM inside of a sample container 116. In some embodiments, the post 102 can be inserted into an ECM. In other embodiments, the post 102 can be in place and the ECM can be poured around the post 102. A sample container 116 can be set into a base 118. In one embodiment, the base 118 securely holds the sample container 116, so that the container will not move when a rotational force is applied to the post 102. The cantilever arm 104 can be moved so that the post 102 can be positioned anywhere within the sample container 116. FIG. 2 illustrates a top down view of an example apparatus for creating stiffness strain-tunable ECMs. FIG. 3 illustrates a side view of an example apparatus for creating stiffness strain-tunable ECMs.

The sample container 116 can hold an ECM. The ECM may or may not contain cells. The ECM can be incubated with the post for a time sufficient to promote adhesion of the ECM to the post 102. In some embodiments, the surface area of the post 102 in contact with the ECM is smaller than the surface area of the sample container 116. After attachment of the ECM to the post 102, the rotation of the post 102 applies a non-uniform strain throughout the ECM.

Figure 4:
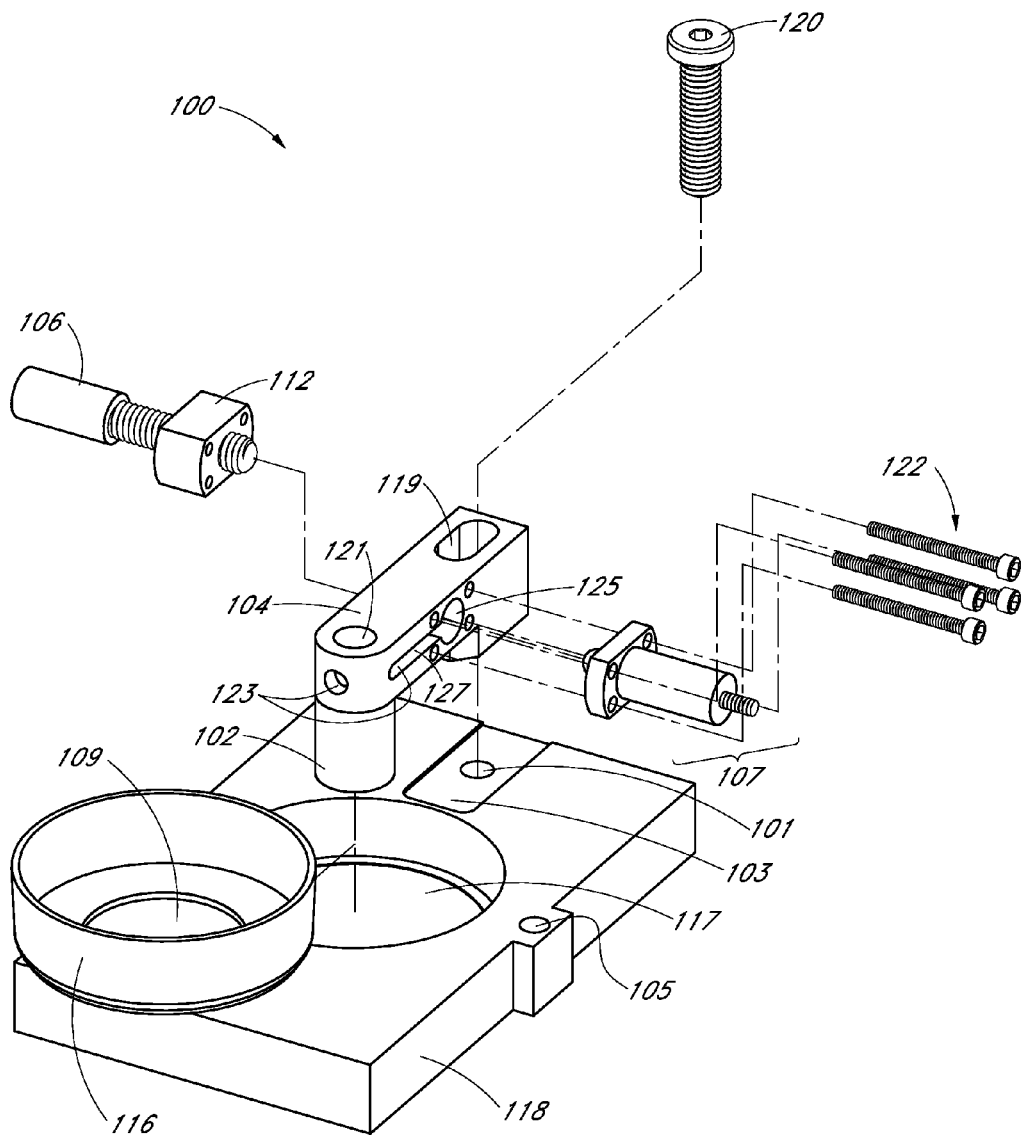
FIG. 4 illustrates a schematic view of an example apparatus for creating stiffness strain-tunable ECMs.

FIG. 4 illustrates a schematic view of an example apparatus for creating stiffness strain-tunable ECMs. The base 118 has a topside and a bottomside and a thickness. In some embodiments, the base 118 is roughly shaped like a rectangle, but other shapes can be used as well. The base 118 is preferably made of aluminum, but can be made of other materials as well. In some embodiments, the base 118 has a depression 103 on the topside for placement of the cantilever arm 104. In some embodiments, there is a screw hole 101 in the depression 103 to allow for attachment of the cantilever arm 104 to the base 118. Other attachment means can be used, such as welding or gluing. In some embodiments, the base 118 has a cavity 117 on the topside sized to fit a sample container 116. Preferably, the cavity 117 of the base 118 is sized to securely hold the sample container 116 so the sample container 116 does not move during operation of the apparatus. In some embodiments, the cavity 117 has a lip at the bottom to securely hold a sample container 116. In some embodiments, the base 118 has at least one hole 105 drilled from the topside to the bottom sized to allow attachment to another object, for example attaching the apparatus 100 with a screw to a table or a microscope.

In some embodiments, the sample container 116 can be, for example, a petri dish or a cell culture dish that fits securely into the cavity 117 of the base 118. In other embodiments, the sample container 116 can be configured to receive and securely hold a dish, for example a petri dish or a cell culture dish. The sample container 116 can comprise a circular area 109 at the base of the sample container 116. The circular area 109 can be an open window or a transparent material so a microscope can be used to view ECM contained in the sample container 116. For example, the circular area 109 can be made of clear plastic or glass. In other embodiments, the sample container 116 can be designed as a specialized petri dish configured to allow ECMs to grow. It could again comprise the circular area 109 described above.

Figure 5:
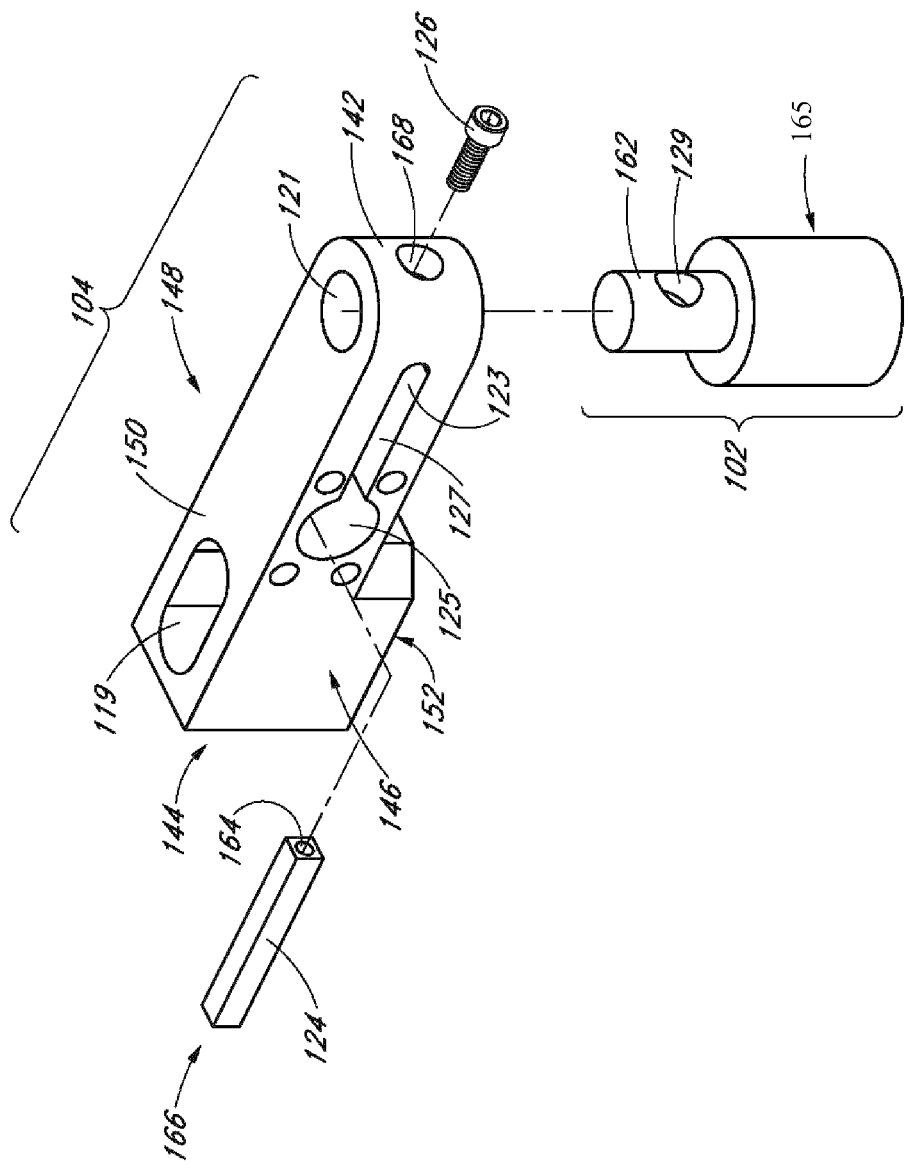
FIG. 5 illustrates a schematic view of an example cantilever arm.

FIG. 5 illustrates a schematic view of an example cantilever arm. Preferably, the cantilever arm 104 is made of Teflon (PTFE). However, the cantilever arm 104 can be made from other materials, and material selection is not limiting. The cantilever arm 104 has a first end 142, a second end 144, a first side 146, a second side 148, a topside 150, a bottomside 152, and a thickness from the topside 150 to the bottomside 152. In some embodiments, the first and second ends 142/144 are rounded. In some embodiments, the first and second ends 142/144 are flat. In some embodiments, one end is rounded and the other end is flat. In some embodiments the topside 150 and bottomside 152 are flat. In some embodiments, the thickness is uniform through the cantilever arm 104. In some embodiments, the thickness is not uniform through the cantilever arm 104.

The cantilever arm 104 can have a cut out hole 119 through the thickness from the topside 150 to the bottomside 152 at the second end 144 so that a screw 120 can be used to join the cantilever arm 104 to the base 118. The hole 119 can be sized and configured to accept a screw so that the cantilever arm 104 is kept steady during operation of the apparatus 100. However, other forms of attaching can be used as well, such as, but not limited to, welding and gluing.

In some embodiments, the cantilever arm 104 can have a cut out hole 121 through the thickness from the topside 150 to the bottomside 152 at the first end 142 so the post 102 can be inserted into the cantilever arm 104. In the illustrated embodiment, the post 102 is cylindrical, although any shape may be used. As illustrated the cylindrical post 102 has a smaller diameter portion 162 configured to fit within the hole 121 in the cantilever arm 104. The smaller diameter portion 162 also has a hole 129 or indentation configured to accept the screw or set pin 126, thereby insuring that the post does not rotate independent from the rotational control means, e.g., bar 124. In the illustrated embodiment, the screw 126 goes through the hole 123 in the cantilever arm 104, through the hole 129 in the smaller diameter portion 162 of the post 102, and threads into a threaded hole 164 in the end of the bar 124. The hole 121 is not limited to a cylindrical shape and size, and can be, for example, shaped like a rectangle, circle, or square; however, in the illustrated embodiment, the hole 121 is cylindrical to allow rotation of the post.

In some embodiments, for example, as illustrated, the cantilever arm 104 has a cavity, or slot, or cut-out 123 spanning the arm for one side to the other, substantially perpendicular to the axis of the post. The cavity may be key-shaped as shown in FIG. 5, with a cylindrical hole 125 and a slot 127 running from the hole 125 toward to first end 142 of the cantilever arm 104. The cavity 123 is configured to accommodate the rotational control means, including the bar 124. The cavity 123 can exit the cantilever arm at the first end 142, the first side 146, and the second side 148, as illustrated. The cavity 123 can comprise a hole 168 at the first end 142 of the apparatus which runs toward the second end 144. The cavity 123 can connect with the cut out hole 121. The hole 168 at the first end 142 of the cantilever arm 104 can be sized and configured to accept a screw 126, thereby connecting the post 102 to the cantilever arm 104. In some embodiments, the cavity 123 does not connect to the cut out hole 119. The cavity 123 can extend out the first 146 and second 148 sides of the cantilever arm 104. In some embodiments, as illustrated, the cavity 123 extending out the sides at the second end 144 is shaped like a circle 125, cut from the first side 146 to the second side 148. In some embodiments, the cavity 123 extends through the cantilever arm 104 towards the front end, shaped like a slot 127 configured so that the lever arm 114 can pass through the slot 127 and extend out from the first side of the cantilever arm 104 to the second side.

The cantilever arm 104 can also have a plurality of screw holes in the thickness sized and configured to accept screws to attach the spring-plunger assembly 107 and the leadscrew 106 on respective opposite sides of the cantilever arm 104. However, other forms of attaching can be used as well, such as, but not limited to, welding and gluing.

The lever arm 114 can comprise a bar 124 and a screw 126. The bar 124 can be generally rectangular and sized to fit within the cavity 123 of the cantilever arm 104. As illustrated, the bar 124 has a threaded hole 164 and a second end 166. The threaded hole 164 of the bar can be configured to accept a screw to hold it within the cantilever arm 104, thereby attaching the post 102 to the cantilever arm 104. The second end 166 of the bar 124 can be located at the second end of the cavity 123, near the circle cut outs 125.

The post 102 is preferably made from implant grade ultra-high molecular weight poly ethylene (UHMWPE), however other materials can be used. The post 102 has a smaller diameter portion 162 and a larger diameter portion 165. In some embodiments, the post 102 is generally cylindrical. In some embodiments, the diameter from the smaller diameter portion 162 tapers to the diameter of the larger diameter portion 165. The smaller diameter portion 162 of the post 102 can be sized to fit within the hole 121 through the thickness from the topside 150 to the bottomside 152 at the first end 142 of the cantilever arm 104. The post 102 can have a hole 129 in the smaller diameter portion 162, perpendicular to the axis connecting the smaller diameter portion 162 with the larger diameter portion 165. The hole 129 can extend through the post 102, and is configured to fit the screw 126 of the cantilever arm 104. The hole 129 can be configured so that it is smaller than the bar 124. The post 102 can be secured within the cantilever arm 104 by inserting the bar 124 into the cavity of the cantilever arm 104 and inserting the screw 126 into the cavity 123 at the first end of the cantilever arm 104, through the hole 129 in the post 102, and screwed into the bar 126. Other means can be used for connecting the post 102 to the cantilever arm 104. In some embodiments, the post 102 is rotated using a gear mechanism.

Figure 6:
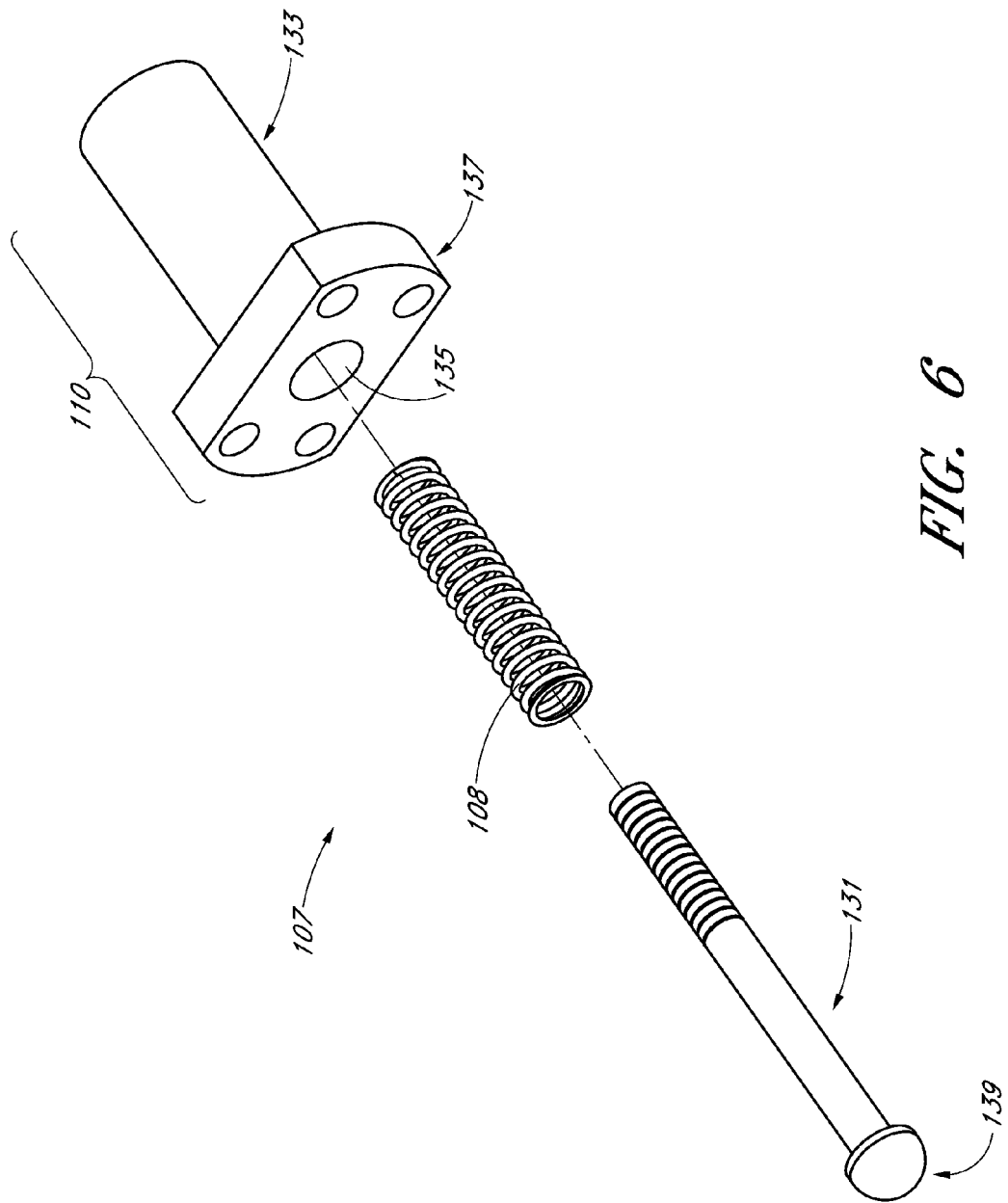
FIG. 6 illustrates a schematic view of an example spring-plunger assembly.

FIG. 6 illustrates a schematic view of an example spring-plunger assembly 107. In some embodiments, for example, as illustrated, a plunger 131 can be inserted through a spring 108. Preferably, the plunger 131 and spring 108 are made from stainless steel, however the material is not limiting. The spring 108 plunger 131 combination can be inserted into a spring holder 110. In some embodiments, the spring holder 110 can have a two part shape. The first part is shaped as a cylinder 133 with a cavity 135 longitudinally through the middle. The cavity 135 can be large enough to fit the plunger 131 and spring 108, but not the plunger head 139. The cylinder 133 can attach to a rectangular portion 137 of the spring holder 110. The cylinder 133 and rectangular portion 137 can be machined together or attached in non-limiting ways such as, but not limited to, gluing and welding. The rectangular portion 137 contains the same cavity 135 as the cylinder 133, and will be large enough to fit the plunger 131 and spring 108, with the head 139 of the plunger 131 extending out of the rectangular portion 137. However, the head 139 of the plunger 131 should be smaller than the circular cavity 125 in the cantilever arm 104 so that the head 139 can enter the cavity 123. The rectangular portion 137 can contain holes so that the spring holder 110 can be attached onto the cantilever arm 104 with screws 122. The spring holder 110 is preferably made from acetal copolymer black, though this material is non-limiting. The spring 108 preferably obeys Hooke's law $$F = -kx$$

where F is the restoring force, k is the spring constant, and x is the displacement of the spring from equilibrium.

As illustrated in FIG. 2, the leadscrew 106 and the spring assembly 107 are positioned so that the head 139 of the plunger 131 and the leadscrew 106 are positioned directly opposite each other with respect to the cantilever arm 104. The head 139 of the plunger 131 and the leadscrew 106 enter the circular cavity 125 in the cantilever arm 104 so that they touch opposite sides of the bar 124 at the end 166. Therefore, when the leadscrew 106 is screwed in, the end 166 of the bar 124 translates towards the plunger 131, thereby compressing the spring 108. The spring 108 will resist translation as the leadscrew 106 is being screwed in. The end of the bar 124 with the thread 164 is attached to the post 102, and can only rotate with the translation of the second end 166, thereby rotating the post 102. The leadscrew 106 can then be unscrewed, and the spring 108 will uncompress and thereby the plunger 131 will translate the end 166 of the bar 124 towards the leadscrew 106, which will cause rotation in the post 102. The spring 108 preferably has a F so that it will translate the plunger 131 to rotate the lever arm 114 against the leadscrew 106 as the leadscrew 106 is being unscrewed. In some embodiments, the rotation of the post 102 is first in one direction, and second in a reverse direction.

In some embodiments, a push rod is used instead of a leadscrew 106. Instead of screwing the leadscrew 106, the push rod can be translated within the cavity of the cantilever arm 104 to actuate the lever arm 114 and rotate the post 102. In some embodiments, the push rod is attached to the lever arm 114 with a bearing mechanism. The spring 108 will still resist the translation of the lever arm 114 and produce a restoring force to keep the lever arm 114 against the push rod when the push rod is translated out of the cantilever arm 104. In some embodiments, the push rod is actuated by a motor. In some embodiments, the push rod is attached to a force meter.

Figure 7:
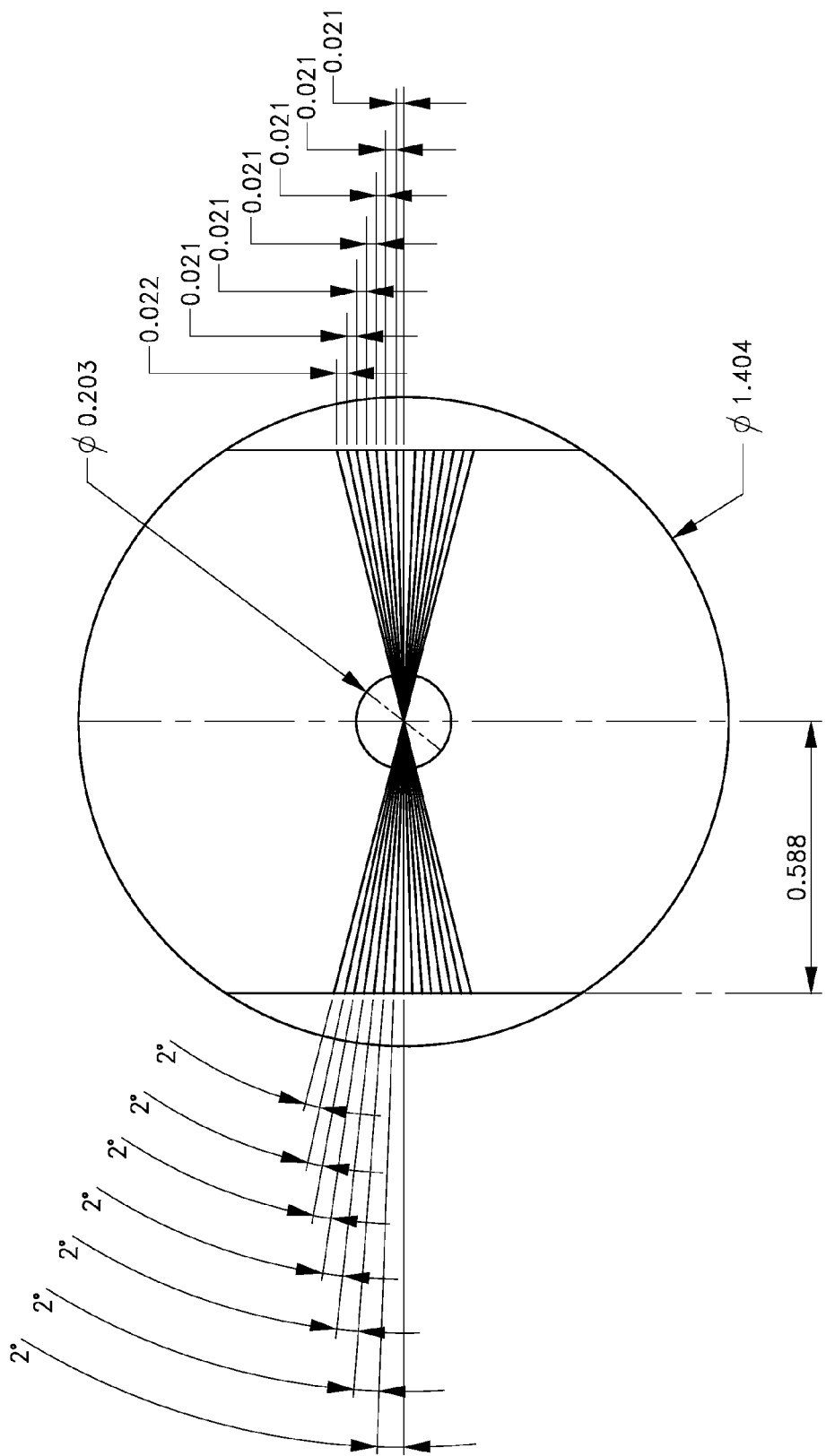
FIG. 7 illustrates the radial rotation of a post vs. the linear actuation (in) of the leadscrew in the described apparatus.

FIG. 7 illustrates the radial rotation of the post 102 as compared to the linear actuation. The lever arm 114 can be rotated to rotate the post 102 in any number of degrees. For example, the post 102 can be rotated about 2° in either direction from the starting position of the post. Every 2° rotation equates to about 0.021 inches of linear actuation. Preferably, the post 102 can be rotated about 2.4° in either direction from the starting position of the post 102. However, the post can be rotated in any number of non-limiting degrees, for example +/−12.5 degrees from the center. In some embodiments the post is rotated a specified degree and then kept at this rotation to induce stress on an ECM.

Figure 8:
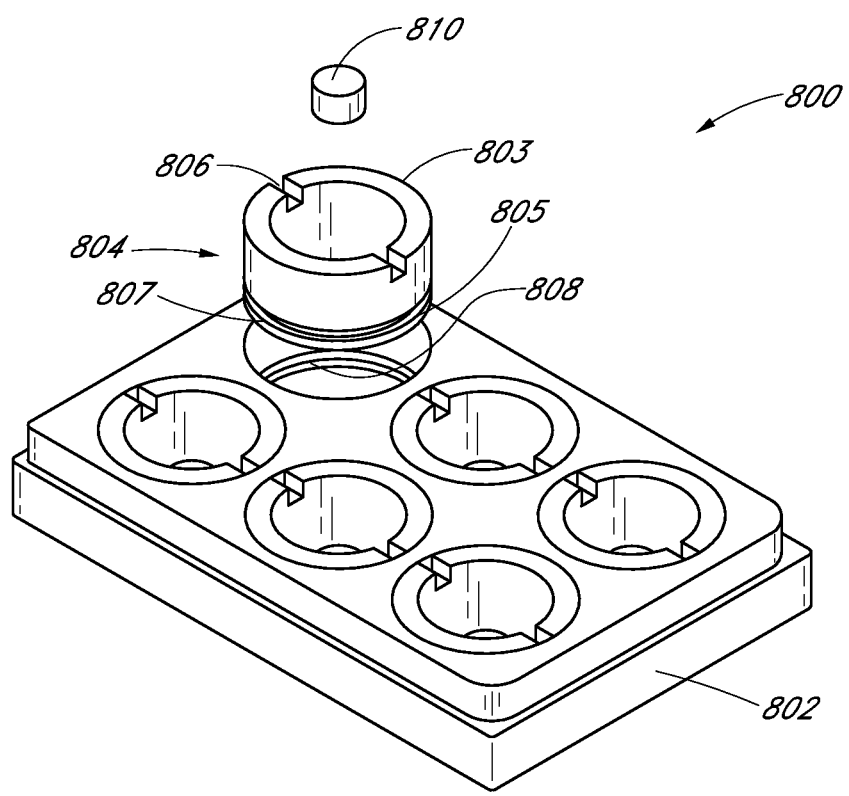
FIG. 8 illustrates an example apparatus for creating stiffness strain-tunable ECMs.
Figure 9:
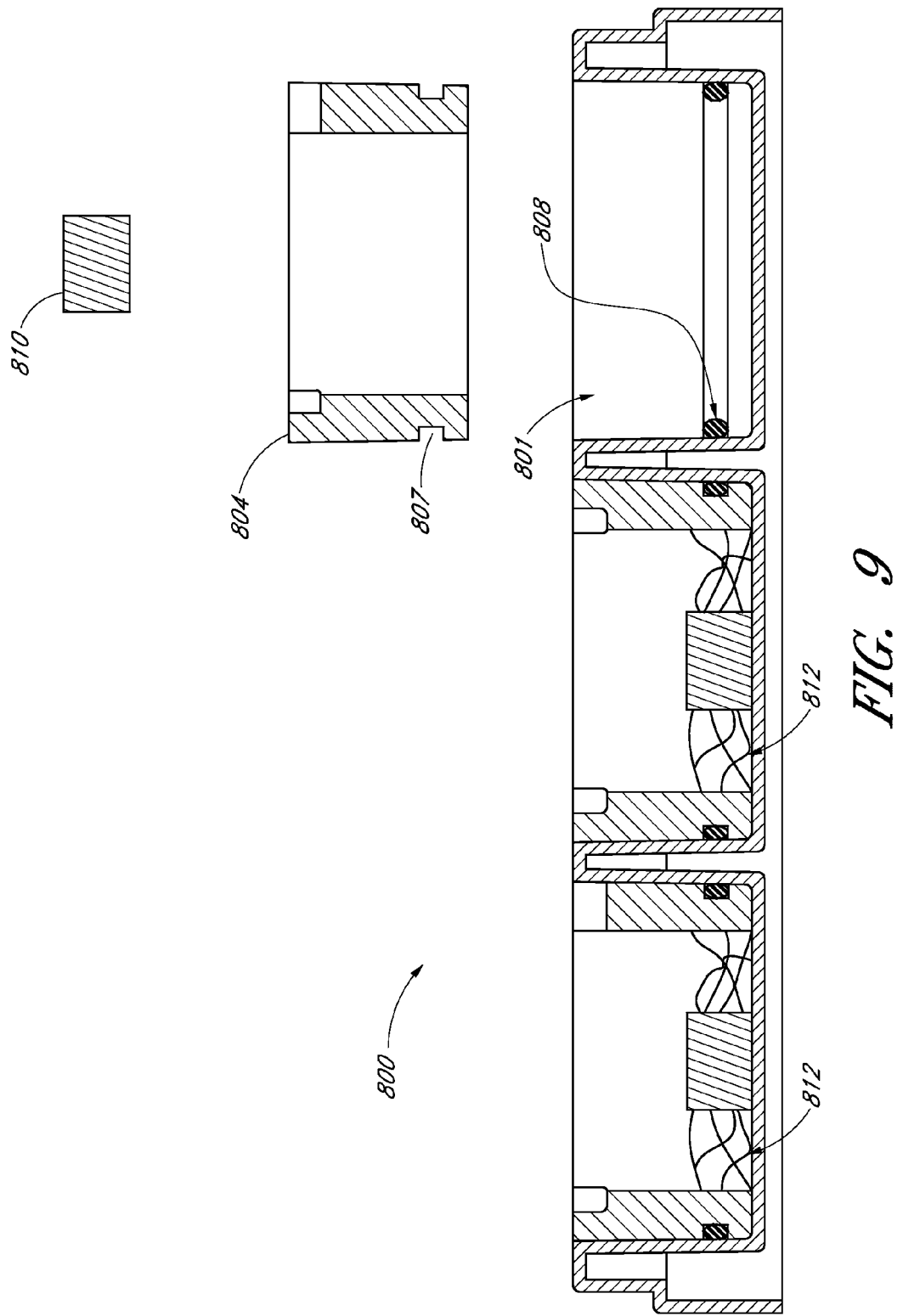
FIG. 9 illustrates a sideview an example apparatus for creating stiffness strain-tunable ECMs.

FIG. 8-9 illustrates an example apparatus for creating stiffness strain-tunable ECMs. FIG. 8 illustrates a top view of the example apparatus 800. The apparatus can contain a base 802. The stage 802 can contain a plurality of circular cavities 801. For example, the base 802 can contain 4, 5, 6, 7, etc. cavities 801. The cavities 801 can be sized and configured to securely hold an outer sleeve 804. The base can be configured to hold an O-ring 808 within the cavity 801.

The outer sleeve 804 can be configured to be able to rotate within the stage 802. The outer sleeve 804 can be generally cylindrical with an opening on one end. The outer sleeve 804 can have a top end 803 and a bottom end 805. The outer sleeve 804 can also have a notch 807 surrounding the sleeve 804 configured to couple with an O-ring 808. In some embodiments, an O-ring 808 is not used. The notch 807 is preferably near the bottom end 805. In some embodiments, the outer sleeve 804 can be, for example, a petri dish or a cell culture dish that fits securely into the cavity 801 of the base 802. In other embodiments, the outer sleeve 804 can be configured to receive and securely hold a dish, for example a petri dish or a cell culture dish. In other embodiments, the sample container can be designed as a specialized petri dish configured to allow ECMs 812 to grow.

In some embodiments, the outer sleeve 804 can contain a plurality of notches 806 on the top end 803. The outer sleeve 804 can fit into the cavities 801 in the base 802, and can be held in place by an O-ring 808, thereby still allowing the outer sleeve 804 to rotate. A fixed central post 810 can be placed in the center of each outer sleeve 804. In some embodiments, the post is cylindrical. However, the shape of the post is non-limiting FIG. 9 illustrates a sideview of an example apparatus for creating stiffness strain-tunable ECMs. As shown, the outer sleeve 804 can be inserted into the circular cavities 801 of the base 802 and supported by the O-ring 808. The post 810 can be placed in the center of the outer sleeve 804. The post 810 can be placed anywhere inside of the outer sleeve 804.

The outer sleeve 804 can hold an ECM 812. In some embodiments, ECM 812 can be poured into the outer sleeve 804 before inserting the post 810 so that the ECM 812 surrounds the post 810 within the outer sleeve 804. In other embodiments, the post 810 can be inserted into the outer sleeve 804 and then the ECM 812 can be poured into the outer sleeve 804. The ECM 812 may or may not contain cells. The ECM 812 can be incubated with the post for a time sufficient to promote adhesion of the ECM 812 to the post 810. In some embodiments, the surface area of the post 810 in contact with the ECM 812 is smaller than the surface area of the outer sleeve 804.

A strain gradient can be applied to the apparatus by rotating the outer sleeve 804 within the base 802. In some embodiments the outer sleeve 804 is rotated by a motor. In some embodiments the outer sleeve 804 is attached to a force meter. In some embodiments, the post 810 remains stationary while the outer sleeve 804 rotates. In other embodiments, the central post 810 rotates. In some embodiments the central post 810 is attached to a motor. In some embodiments the central post 810 is attached to a force meter.

The outer sleeve 804 or post 810 can be rotated in any number of degrees. A bar can be inserted into the notches 806 on the outer sleeve 804. The bar can then be rotated by attaching it to, for example, a motor. For example, the outer sleeve 804 or post 810 can be rotated about 2° in either direction from the starting position of the outer sleeve 804 or post 810. Preferably, the outer sleeve 804 or post 810 can be rotated about 2.4° in either direction from the starting position of the outer sleeves 804. However, the outer sleeve 804 or post 810 can be rotated in any number of non-limiting degrees. The outer sleeve 804 or post 810 can be first rotated in one direction, and second in the reverse direction.

In some embodiments, the outer sleeve 804 can be rotated by inserting a lever, e.g. a handle or bar, across the top end 803 of the outer sleeve 804. The lever can then be rotated by, for example, manual movement of the lever, a wrench, a direct motordrive, or a belt-drive, thereby rotating the outer sleeve 804. In some embodiments, the outer sleeve 804 could have tabs extending out. The tabs could be removable or fold away. The tabs can then be rotated by, for example, manual movement of the lever, a wrench, a direct motordrive, or a belt-drive, thereby rotating the outer sleeve 804. A wrench, a direct motordrive, or a belt-drive could fit into the notches 806 of the outer sleeve 804, thereby rotating the outer sleeve 804.

In some embodiments, the outer sleeve 804 protrudes from the base 802. The outer sleeve 804 could then be rotated manually or by belt actuation of a belt in contact with the outer sleeve 804 outside of the base 802.

In some embodiments, the notches 806 in the outer sleeve 804 could have a tooth/ratcheting mechanism.

In some embodiments, a cover can be placed over the outer sleeve 804 which interlocks with the outer sleeve 804. In some embodiments, the cover comprises a mechanism that interlocks with the outer sleeve 804. The cover or mechanism can be rotated to thereby rotate the outer sleeve 804.

Figure 10:
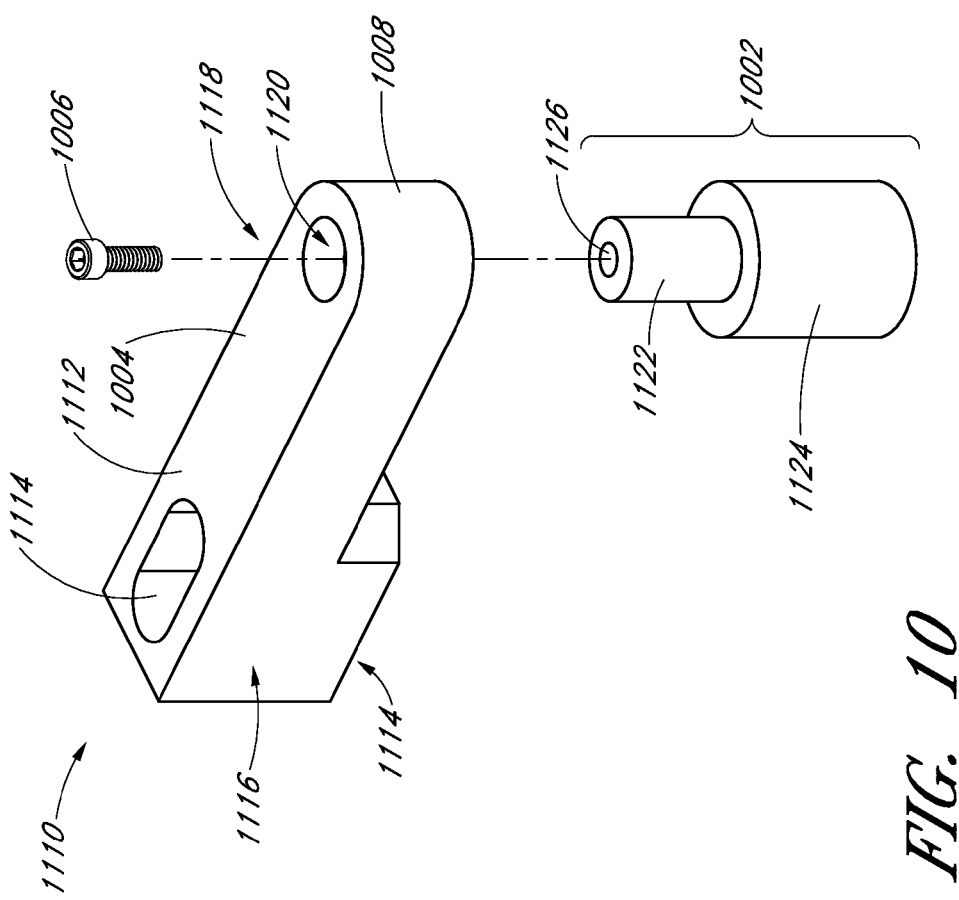
FIG. 10 illustrates a schematic view of an example cantilever arm.

FIG. 10 illustrates a schematic view of an example cantilever arm. Preferably, the cantilever arm 1004 is made of Teflon (PTFE). However, the cantilever arm 1004 can be made from other materials, and material selection is not limiting. As illustrated, the cantilever arm 1004 has a first end 1008, a second end 1010, a topside 1012, a bottomside 1014, and a thickness from the topside 1012 to the bottomside 1014. In some embodiments, the first and second ends 1008/1010 are rounded. In some embodiments, the first and second ends 1008/1010 are flat. In some embodiments, one end is rounded and the other end is flat. In some embodiments the topside 1012 and bottomside 1014 are flat. In some embodiments, the thickness is uniform through the cantilever arm 1004. In some embodiments, the thickness is not uniform through the cantilever arm 1004.

The cantilever arm 1004 can have a cut out hole 1114 through the thickness from the topside 1012 to the bottomside 1014 at the second end 1010 so that a screw 120 can be used to join the cantilever arm 1004 to the base 118. The hole 1114 is sized and configured to accept a screw so that the cantilever arm 1004 is kept steady during operation of the apparatus 100. However, other forms of attaching can be used as well, such as, but not limited to, welding and gluing.

In some embodiments, the cantilever arm 1004 can have a cut out hole 1120 through the thickness from the topside 1012 to the bottomside 1014 at the first end 1008 configured so the post 1002 can be inserted into the cantilever arm 1004. The hole 1120 is not limited to a shape and size and can be, for example, a rectangle, circle, or square.

The post 1002 is preferably made from implant grade ultra-high molecular weight poly ethylene (UHMWPE), however other materials can be used. The post 1002 has a smaller diameter portion 1122 and a larger diameter portion 1124. In some embodiments, the post 1002 is generally cylindrical. In some embodiments, the diameter from the smaller diameter portion 1122 tapers to the diameter of the larger diameter portion 1124. The smaller diameter portion 1122 of the post 1002 can be sized to fit within the hole 1120 and to mate with a ratcheting mechanism within the hole 1120. The post 1002 can have a hole 1126 in the center of the smaller diameter portion 162 in the axial direction from the smaller diameter portion 1122 to the larger diameter portion 1124 configured to mate with a device such as, for example, a screwdriver. However, other devices can be used. The post 1002 can be secured within the cantilever arm 1004 so that the post 1002 can still rotate within the cantilever arm 1004. In some embodiments, the post 1002 can connect to the cantilever arm 1004 within the hole 1120 through a ratcheting mechanism. When the hole 1126 is turned by a screwdriver, the ratcheting mechanism only allows a certain amount of movement. Therefore, the ratcheting mechanism can be set to a radial movement of about 2° in either direction from the starting position of the post 1002, preferably about 2.4°, and the post 1002 can be rotated by a device such as a screwdriver. In some embodiments, the post 1002 is rotated using a gear mechanism.

EXAMPLES

Figure 11:
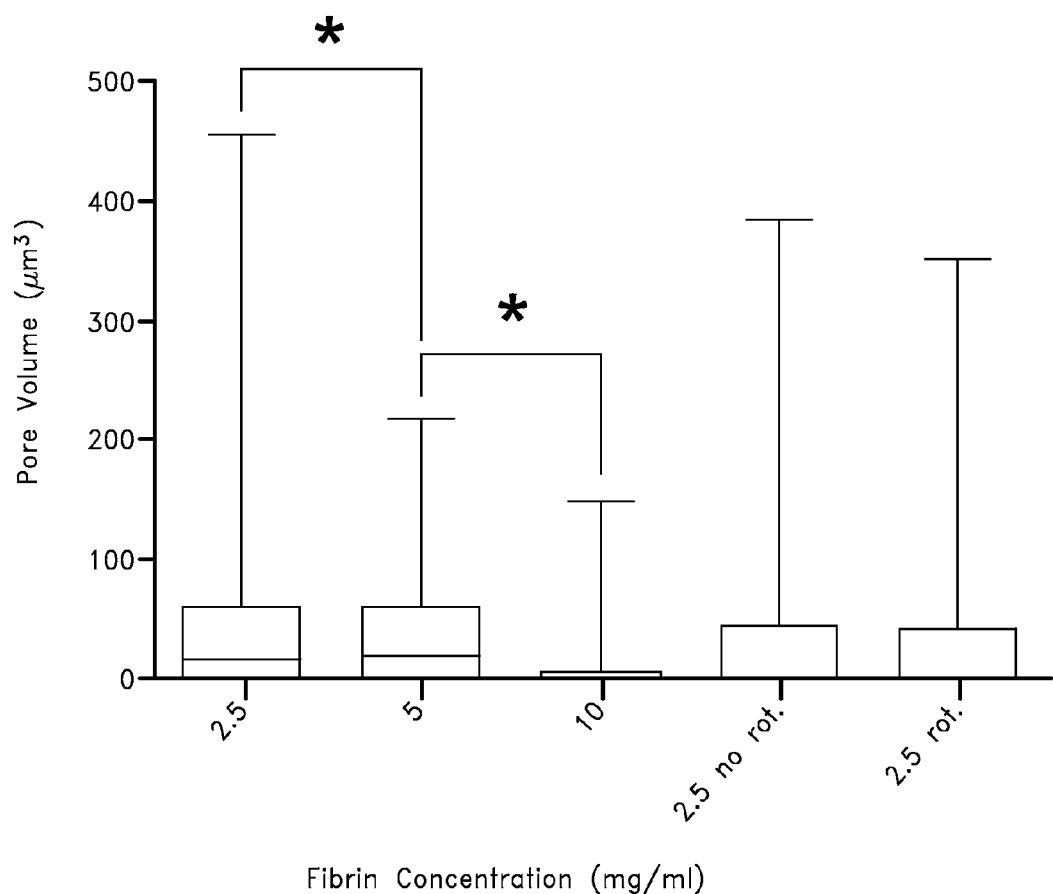
FIG. 11 illustrates a comparison of fibrin pore volume.

The stiffness of the ECM and the impact of the strain on the ECM and any cells in the ECM may be measured by the following techniques parallel plate rheology, active microrheology, and orbital tracking methods. These methods do not encompass all the methods that may be used to measure stiffness of the ECM and/or the impact of strain on the ECM and the cells contained in the ECM. Comparison of fibrin pore volume in FIG. 11 shows significant pore volume reduction with increasing fibrin concentration. In using the apparatus to apply strain on the ECM, an unexpected ten-fold stiffening of the ECM within the 2.5 mg/ml gel was observed. However, as shown in FIG. 11, the pore volume did not change.

Fibrin Hydrogels

Bovine fibrinogen (Sigma) solutions (2.5, 5, or 10 mg/ml) were prepared in 1×PBS or plain basal media under sterile conditions. In gels prepared for active microrheology (AMR), 20 µl of a 20 µg/ml solution of 2 µm diameter silica beads and 50 µl fetal bovine serum (FBS) were mixed with the sterile-filtered fibrinogen solution for every 1 ml of gel. 1 ml of this final gel solution was added to 20 µl of polymerization-initiating thrombin (50 U/ml) previously aliquoted into a 35 mm glass bottom Petri dish. FBS contains factor XIII, a zymogen that contributes to the cross-linking of the fibrin gel when activated to by thrombin. Acellular solutions were left undisturbed for 30 min at room temperature until gelation was complete. For cell-seeded fibrin, cells were incorporated along with microrheology beads and FBS, and gelation was completed in a standard cell culture incubator. To maintain gel hydration, 2 ml of PBS or media were added to the dish after gelation. Fluorescent fibrin gels were constructed with a 1:10 ratio of fluorescent Alexa-488 fibrinogen to non-fluorescent fibrinogen.

Parallel Plate Rheology

Curing and mechanical characterization of the gel was accomplished in situ on an AR G2 rheometer equipped with a Peltier stage and configured with a 20 mm stainless steel parallel plate attachment. The Peltier stage was cooled to 4° C. after which 320 µl of fibrinogen solution at 2.5, 5 or 10 mg/ml was injected into a 1050 µm gap between the plate and stage. The edge of the plate was sealed with silicone oil to prevent evaporation, and the top plate was lowered to 1000 µm. The temperature was increased from 4° C. to 37° C. over five minutes and then held at 37° C. for 45 minutes. Rheology was performed throughout the clotting at 1% strain and 1 rad/sec to confirm full gelation after 45 minutes as indicated by a plateau in the measure of the shear modulus, G'. After gelation, G' was measured by a frequency sweep from 1 to 100 rad/sec at 1% strain. Strain sweeps were performed from 0.001 to 10% strain at a constant frequency of 1 radian/s. Five gels were measured at each concentration of fibrinogen for each measurement set.

Active Microrheology Instrumentation

Figure 12:
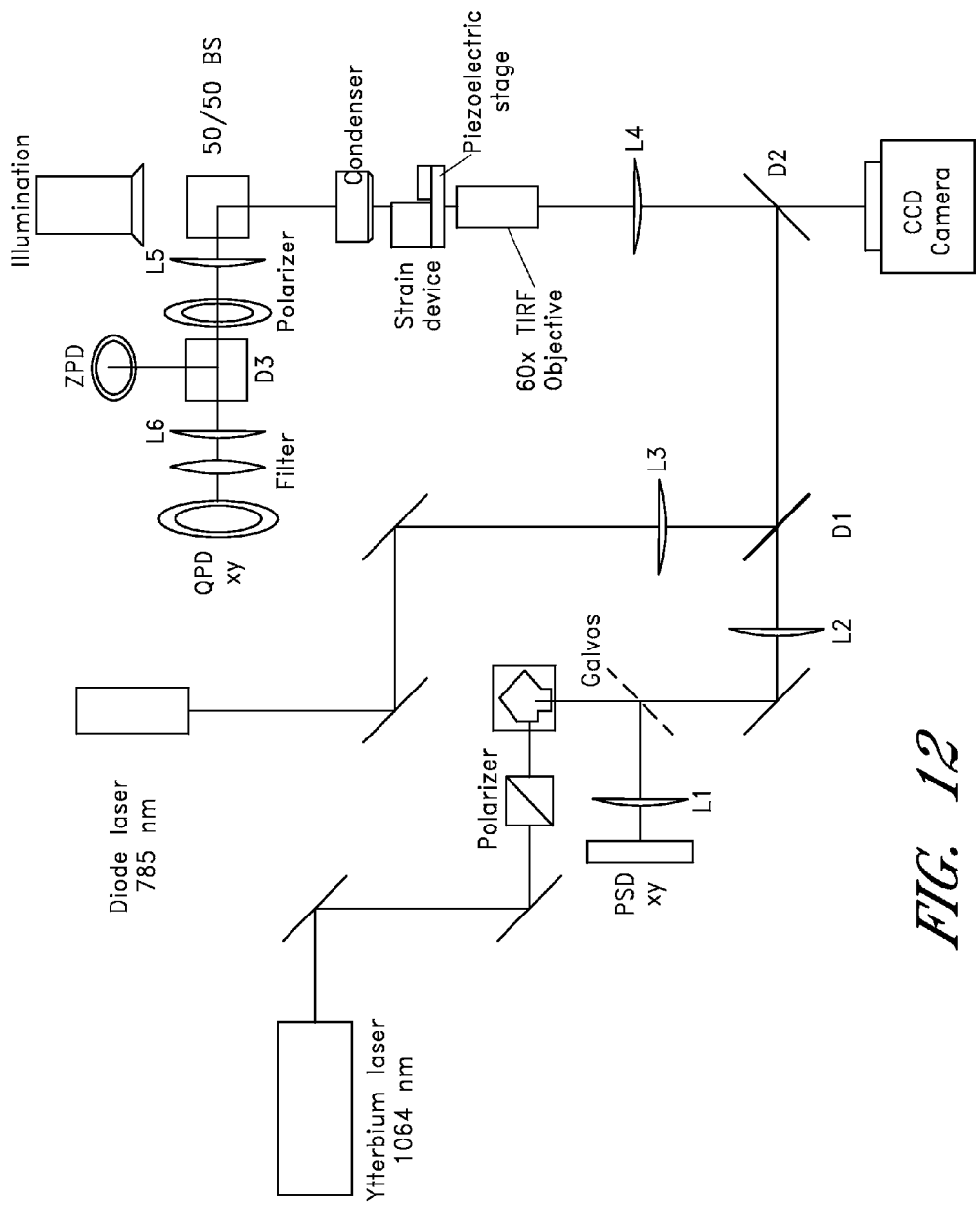
FIG. 12 illustrates an optical instrumentation which can be used for AMR.

FIG. 12 illustrates an optical instrumentation which can be used for AMR is an expansion of a passive microrheology instrument diagramed. The instrument is a custom modified Olympus IX81 inverted microscope mounted on a vibration dampening SMART table. Trapping is achieved by a 1064 nm Ytterbium fiber laser (IPG) steered by XY scanning galvanometer mirrors. The trapping beam is expanded by lenses L2 (f=400 mm) and L4 (f=500 mm) and focused into the sample by a PlanApo 1.45 NA 60X oil immersion objective. A 30 mW 785 nm diode laser is expanded by lenses L3 (f=150) and L4 (f=500 mm) for particle position detection. The two laser beams are combined by a dichroic beamsplitter D1 and mixed into the microscope imaging path by a short-pass dichroic D2. The trapping beam is partially reflected by a microscope cover glass and focused by L1 (f=50 mm) onto an XY position sensitive photodiode to monitor the position of the beam during scanning. Forward scattered 785 nm light is refocused by lenses L5 (f=50 mm) and L6 (f=35 mm) onto a quadrant photodiode (QPD) positioned conjugate to the back focal plane of our objective lens, while forward scattered 1064 nm light is reflected by a short-pass dichroic D3 to overfill a photodiode (ZPD) for z-position detection. The ZPD was not implemented in this study.

2 µm diameter beads were appropriate for microrheology in 2.5, 5, and 10 mg/ml fibrin gels. A sinusoidal optical trap oscillated microbeads embedded within fibrin gels. An oscillating microbead steers the detection laser across the QPD, which outputs three analog signals: diff(X), diff(y), and sum. PSD and QPD signals were sampled at 10 kHz for 5 seconds by a multifunction data acquisition board (M-series DAQ). The X and Y signals were normalized by the sum signal to compensate for small changes in average laser intensity. For each bead, five replicate signals were collected at 5, 10, 20, 50, 100, and 200 Hz, for an oscillation amplitude of 60 nm. Hardware and data acquisition were controlled via custom LabVIEW software.

Active Microrheology Calibration

PSD signals were calibrated by imaging the partial back reflection of the trapping beam as it was steered across a stage micrometer. QPD signals were calibrated by transversely sweeping a laser-trapped 2 µm bead through the focus of the 785 nm detection beam in a stepwise manner (5 nm per step). From calibration experiments it was determined that QPD signals were linear with respect to bead displacement if displacements were less than 150 nm. Optical trap stiffness was 30.3±0.5 pN/µm as determined by a power spectrum method.

Active Microrheology Analysis

The forcing function acting on a bead was calculated from calibrated laser and bead position signals as described by Brau et al., "Passive and active microrheology with optical tweezers," Journal of Optics A: Pure and Applied Optics: 5103-5112, hereby incorporated by reference in its entirety. The laser trap position function given by $$x_t(t) = A_t \sin(\omega t)$$

is obtained from the Fourier transform of the calibrated PSD signal, where $A_t$ is the amplitude of the transform at the forcing frequency $\omega$. The bead oscillation function given by $$x_b(t) = A_b \sin[\omega t - \theta_b(\omega)]$$

is obtained from the Fourier transform of the calibrated QPD signal, where $A_b$ is the bead oscillation amplitude and $\theta_b(\omega)$ is the phase lag induced by material resistance. The forcing function acting on the bead is calculated from the difference between $x_t(t)$ and $X_b(t)$ $$x_f(t) = x_t(t) - x_b(t) = A_f \sin[\omega t - \theta_f(\omega)]$$

where $A_f$ is the amplitude of the forcing function and $\theta_f(\omega)$ is the phase lag between $x_t(t)$ and $x_f(t)$.

Figure 13:
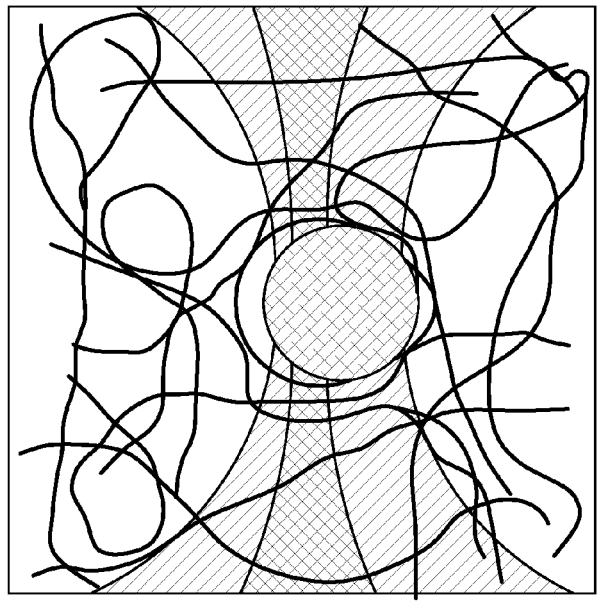
FIG. 13 illustrates an oscillating bead in a matrix.

As previous described by Mizuno et al., "Active and Passive Microrheology in Equilibrium and Nonequilibrium Systems. Macromolecules," hereby incorporated by reference in its entirety, the apparent complex response function $A(\omega)$, which includes the contribution from trapping forces is $$A(\omega) = \frac{x_b(\omega)}{x_f(\omega)}$$

where $x_b(\omega)$ and $x_f(\omega)$ are the Fourier transforms of $x_b(t)$ and $X_f(t)$ respectively. If the total laser trap contribution k is $$k = k_t + k_b$$

where $k_t$ is the stiffness of the trapping beam, and $k_b$ is the stiffness of the detection beam, then the corrected response function $\alpha(\omega)$ is $$\alpha(\omega) = \frac{A(\omega)}{1 - kA(\omega)}$$

which effectively removes the contribution of optical forces from the measured material properties. Thus, the complex shear modulus $G(\omega)$ given by $$G(\omega) = G'(\omega) + G''(\omega)$$

can be calculated from $\alpha(\omega)$ by $$G(\omega) = \frac{1}{6\pi a \alpha(\omega)}$$

where '$\alpha$' is the radius of the bead. An oscillating bead does work on the local matrix as shown in FIG. 13, which can either elastically store energy or dissipate it through viscous losses. The elastic and viscous nature of the matrix surrounding a bead is represented by the real and imaginary components of $G(\omega)$ respectively.

Figure 14:
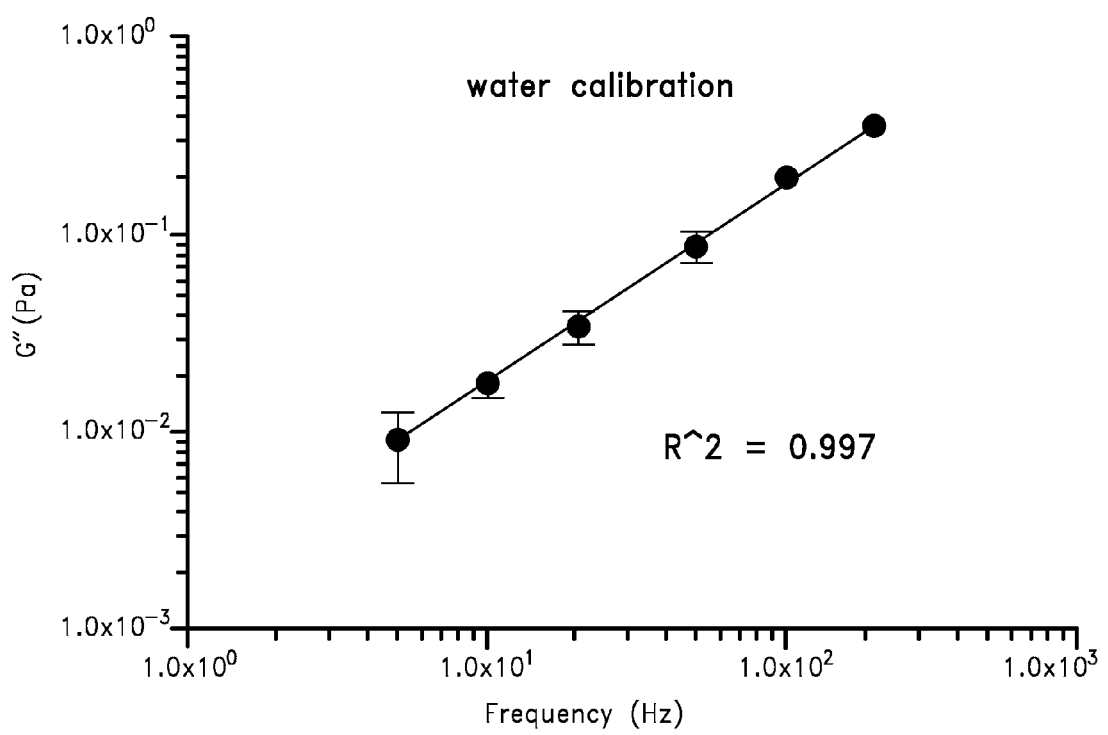
FIG. 14 illustrates system performance in water.

The system performance was validated prior to each experiment by measuring the shear modulus spectra of water, as shown in FIG. 14.

Smooth Muscle Cell Culture in 3-D Fibrin Hydrogels

Primary human aortic smooth muscle cells (AoSMC) were cultured in SmBM Basal Media supplemented with a SmGM-2 BulletKit at 37° C. and 5% CO2. The BulletKit contains 5% (v/v) fetal bovine serum, 0.2% (v/v) human basic fibroblast growth factor, 0.1% (v/v) insulin, gentomycin/amphotericin, and human epidermal growth factor. AoSMC-seeded fibrin gels for microrheology experiments were constructed by first dissolving fibrinogen in FBS-free media and then adding cells at 50,000 cells per 1 ml. Gelation was initiated as described above and cells between passages 5 and 7 were used for all experiments. For strain gradient device experiments, cells were cultured in 2.5 mg/ml fibrin gels at 500,000 cells/ml in media supplemented with epsilon-amino-N-caproic acid (e-ACA) at 3 mM to inhibit plasmin mediated fibrin gel degradation. Strain gradients were induced on day 2 and on day 9 gels were formalin fixed and stained for F-actin with Alexa-488 phalloidin per the manufacturer's protocol (Invitrogen).

Finite Element Model of Shear Strain

A Finite Elements Analysis (FEA) was performed with the commercial software ABAQUS to calculate strain profiles along radial and circumferential paths. The modeling space was two-dimensional, with plane stress conditions. The walls of the dish and the plug were each modeled with 200 discrete rigid elements, whereas the gel was modeled with 4600 quadratic solid elements, with reduced integration. The gel was tied to both boundaries and assumed to behave as a hyperelastic, neo-hookean solid, with a Poisson's ratio of 0.8, and a true stress-true strain curve in agreement with Winer et al, "Non-linear elasticity of extracellular matrices enables contractile cells to communicate local position and orientation," PLoS One 4: e6382, hereby incorporated by reference in its entirety. The dish wall was fixed and the plug was rotated 2.4° counterclockwise about its center point, while being constrained in the radial direction.

Scanning Confocal Microscopy

Scanning confocal microscopy was performed using a fluoView1000 microscope equipped with a 10X air objective and a 60X, 1.2 NA UPLSAPO water immersion objective. Samples were excited by a 488 nm Argon laser and imaged using standard FITC filters.

Fibrin Mesh Analysis

Pore size distributions of fluorescently labeled fibrin gels were obtained from confocal image stacks using a 100 nm step size. Confocal image stacks were reconstructed and segmented in 3D using Volocity, a volumetric analysis software package. The software identifies all touching objects (fibers) within a user defined 3D region of interest (ROI) and segments discrete yet adjacent pores. A lower volume threshold of 0.01 urrr' was applied. Three ROIs containing approximately 500 pores were analyzed per gel.

3D Fiber Imaging and Tracking System

All 3D fibrin fiber imaging and tracking experiments were performed on a custom built two-photon microscope based on an inverted IX70 Olympus microscope, similar to the one described previously. For excitation, a mode-locked 80 MHz Ti: Sapphire laser with an integrated Verdi pump source was used. Laser pulses were 150 fs in width, laser average intensity was approximately 150 µW at the sample position, and excitation wavelength was 790 µm for all the tracking experiments. An UPlanFL N 60X 0.9 NA air objective and a shortpass dichroic mirror were used to direct the excitation light into the sample. Additionally a HQ700LP filter was positioned before the dichroic to filter out the Ti: Sapphire fluorescence. Three-dimensional scanning was obtained using galvanometer motor-driven scanning mirrors with controller series 603X servo system, and a PIFOC P-721 piezo-driven objective device. Both the galvanometer and piezo were driven by an ISS 3-axis card. Fluorescence signal from the fibers was detected with a photomultiplier tube through an emission filter. Finally, signal was amplified, discriminated, and TTL pulses were counted by the ISS 3-axis data acquisition card. Experiments were controlled by a commercially available data acquisition program.

Orbital Tracking Method

The orbital tracking method has been previously described. Briefly, during each cycle of the tracking routine, the excitation beam traces a circular orbit in a given position around the fiber. The orbit's radius is equal to half the waist of the microscope point spread function (PSF). In the experiments reported in this work, each orbit is in the x-z plane and takes 8 ms. The acquisition rate was chosen such that 128 points are measured during each orbit. After each cycle of the tracking routine, the DC value, AC value, and phase of the first harmonic was calculated by the Fast Fourier Transform (FFT). The modulation (defined as the ratio AC/DC) varies monotonically as the distance from the fiber to the center of the orbit is increased. For every measured value of modulation, the distance of the fiber's center of mass from the center of the orbit to determine the coordinates of the fiber can be calculated. The center of the orbit is relocated to the calculated center of mass. In other words, during the tracking routine the scanner follows the fiber's center of mass by changing its position to that calculated in the previous cycle. When the fiber position is determined with respect the x-z plane, the orbit is moved according to a linear ramp function incrementing the orbit position in the y-direction along the fiber and a new cycle of the tracking routine starts. Given the highly branched nature of the fibrin network, it is possible that tracking can erroneously deviate from one fiber to a neighboring fiber. As a control, orbit coordinates and fluorescence intensity as a function of time are analyzed after tracking is complete. If the tracking jumps to a neighboring fiber, there will be an abrupt change in the modulation of the first harmonic and a spike in the intensity. Fibers were tracked a maximum distance of 10 μm over 120 seconds with a step size resolution of 56 nm. All measured fibers were located at least 3 μm above the cover slip to avoid surface effects. The y-position of the orbit was sequentially moved through approximately 1500 positions along each fiber. For display, the line shape of the reconstructed trajectory changes every 100 measured points.
Statistical Analysis.

All data are expressed as mean and standard deviation. T-tests was used to test differences between means with a level of significance of 0.05, unless otherwise indicated.
Results
AMR Reveals Mechanical Heterogeneity of Fibrin Gels Both AMR and parallel plate macrorheology were used to measure complex shear moduli in fibrin gels polymerized from 2.5, 5, and 10 mg/ml solutions of fibrinogen. AMR of fibrin gels measures a large variation in stiffness between micro domains in a single gel, while macrorheology measures an ensemble average, which is insensitive to the distribution in micro domain stiffness. Therefore, parallel plate rheology fails to report local heterogeneities in gel stiffness detectable by AMR. Agreement was found between macro and microrheology of 2.5 mg/ml fibrin gels, but not for 5 mg/ml and 10 mg/ml fibrin, where microrheology reports a softer matrix than macrorheology (Table 1). Both rheology techniques report elastic shear moduli increasing linearly with fibrin concentration (macro: $r^2=0.98$, micro: $r^2=0.97$), although nonlinearities would be observed at higher strains.

Figure 15A:
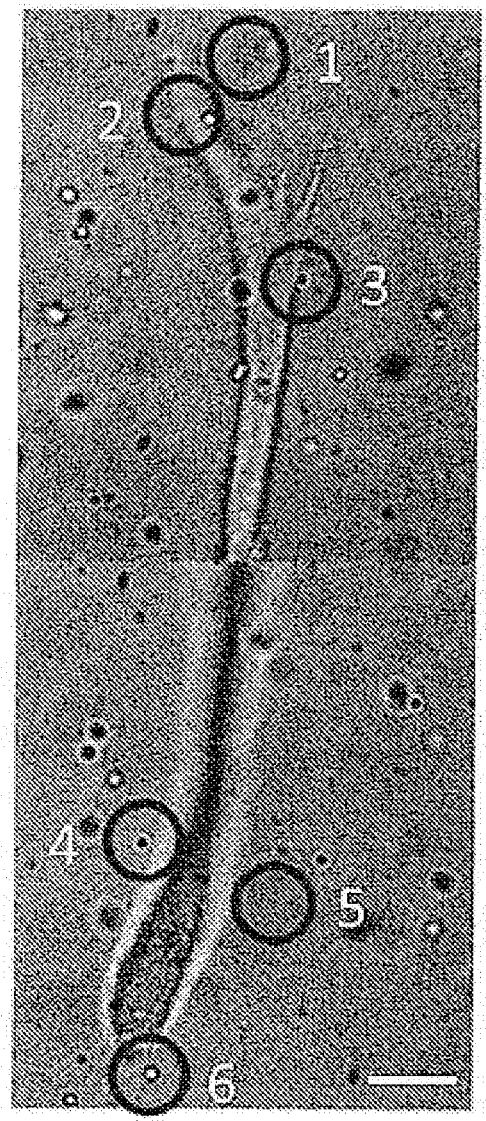
FIG. 15A-C illustrates the variability of local stiffness of an AoSMC.
Figure 15B:
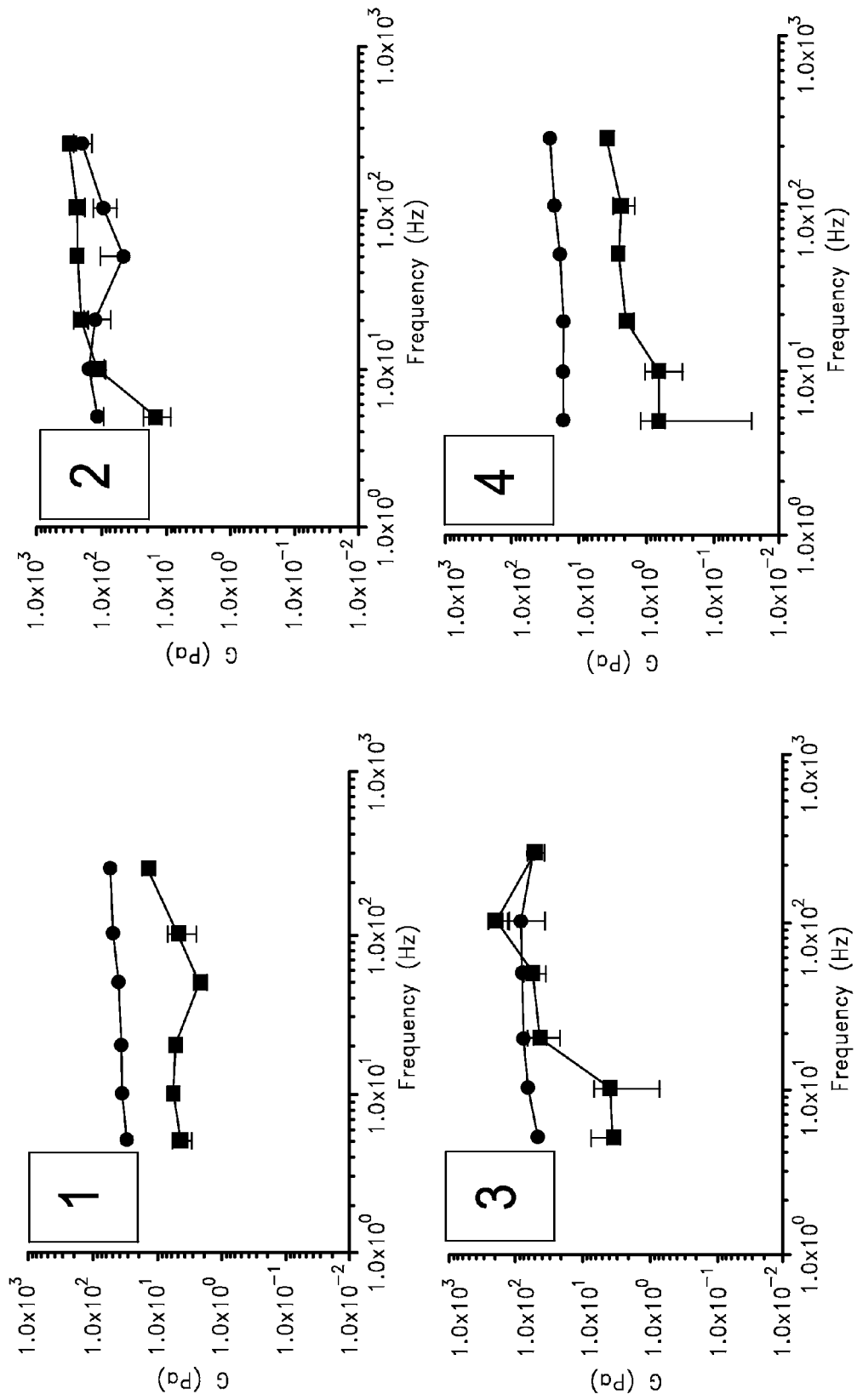
Figure 15C:
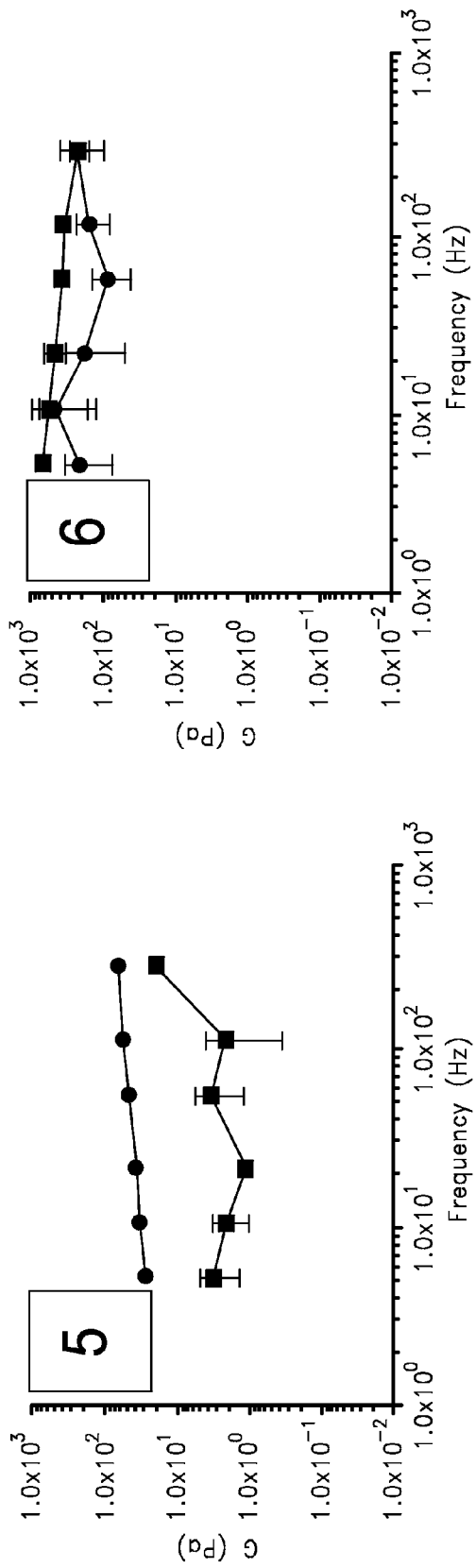

The importance of measuring local stiffness is highlighted in FIG. 15A-C, in which the material stiffness varies by a factor of 10 around the periphery of a single AoSMC cultured in a 3D fibrin gel, an observation not detectable by macrorheology. Furthermore, regions measured at the polar contracting ends of the cell (beads 2 and 6) are noticeably stiffer than those regions located along the length of its body (beads 3-5).

TABLE 1

Comparison of fibrin parallel plate and microrheology

| [Fibrin] (mg/ml) | G' macro (Pa) | G' AMR (Pa) | p-value |
|---|---|---|---|
| 2.5 | 18 ± 2.5 | 13 ± 20 | 0.45 |
| 5 | 90 ± 7.6 | 43 ± 35 | <0.05 |
| 10 | 377 ± 30 | 186 ± 182 | <0.05 |

AMR in the Strain Gradient Device: Spatially Dependent Stiffening

Figure 16:
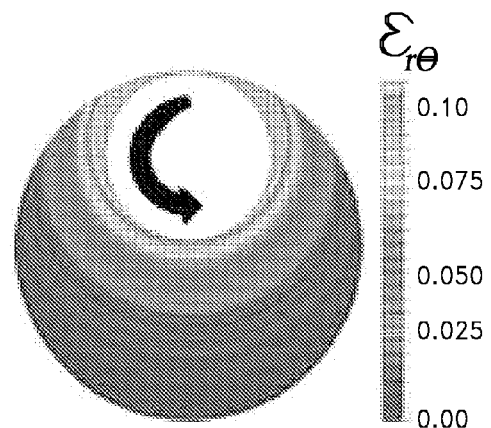
FIG. 16 illustrates a non-uniform distribution of shear strain.
Figure 17:
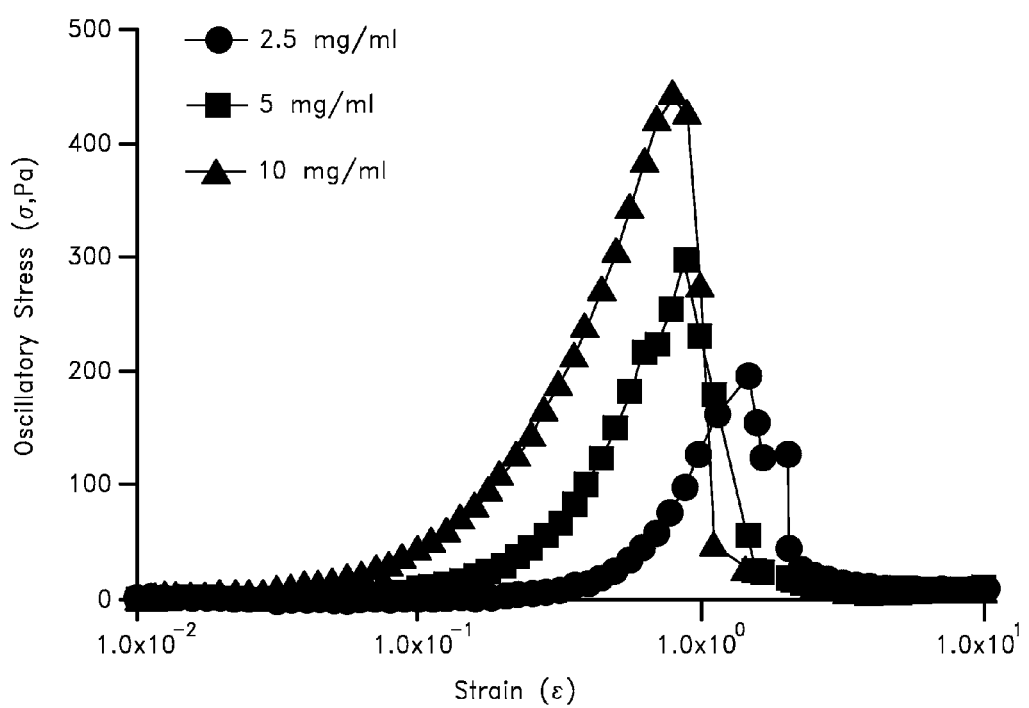
FIG. 17 illustrates the non-linear stress strain characteristics of different fibrin concentrations.

In the apparatus, local gel stiffness was modulated by rotation of the post as measured in situ by AMR. The stiffness may be modulated independent of initial fibrinogen concentration following a 2.4° rotation of the post within a 2.5 mg/ml fibrin gel. For these conditions, FEA estimates a nonuniform distribution of shear strain within the Petri dish, shown in FIG. 16. Strain is greatest at the gel-post interface, decreasing radially in a steep gradient towards the edge of the dish. The eccentric placement of the post within the dish induces a large variation in strain ranging from 0.005 to 1.3, as shown in FIG. 17.

Figure 18:
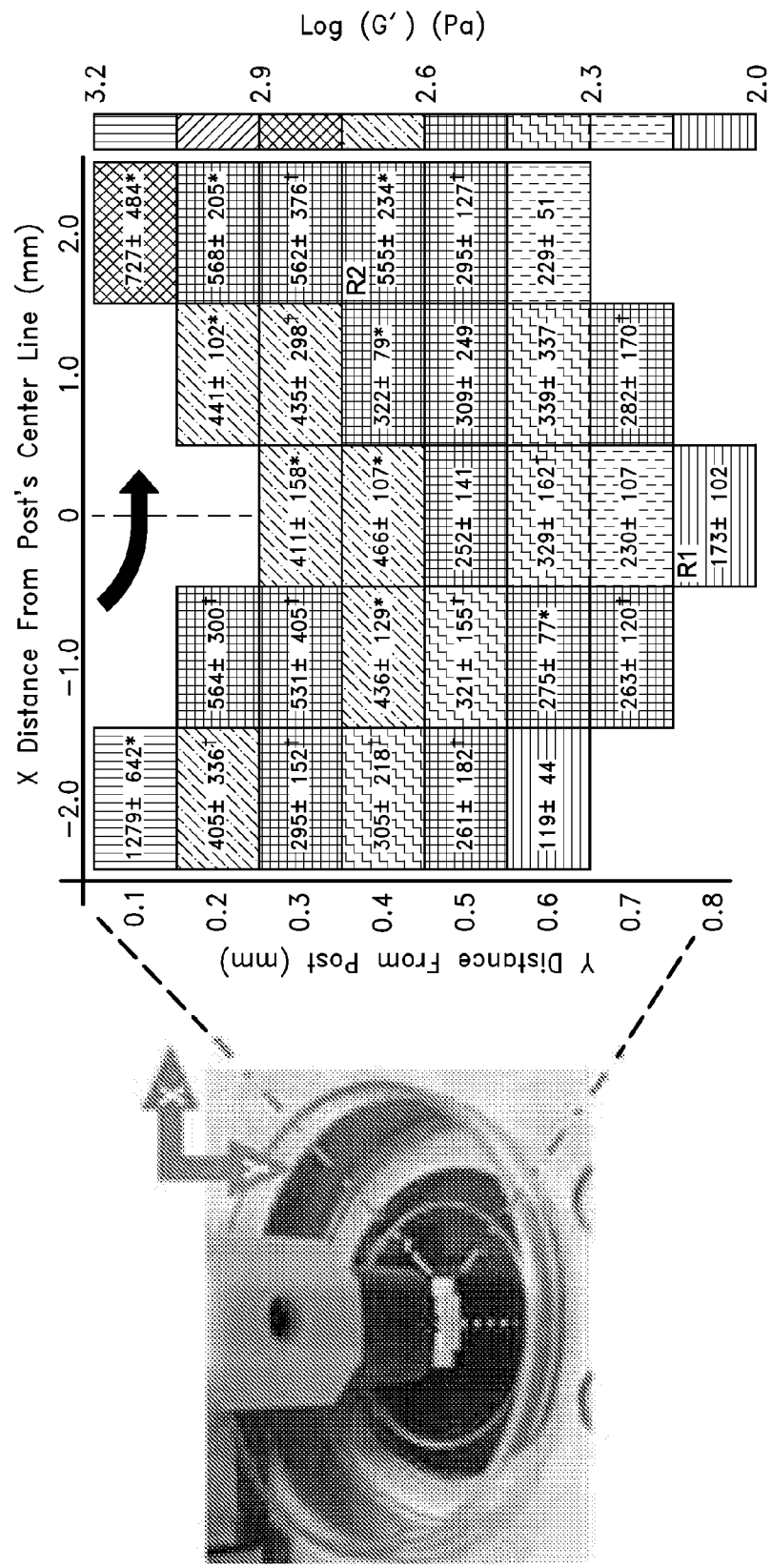
FIG. 18 illustrates AMR within regions of a gel.
Figure 19:
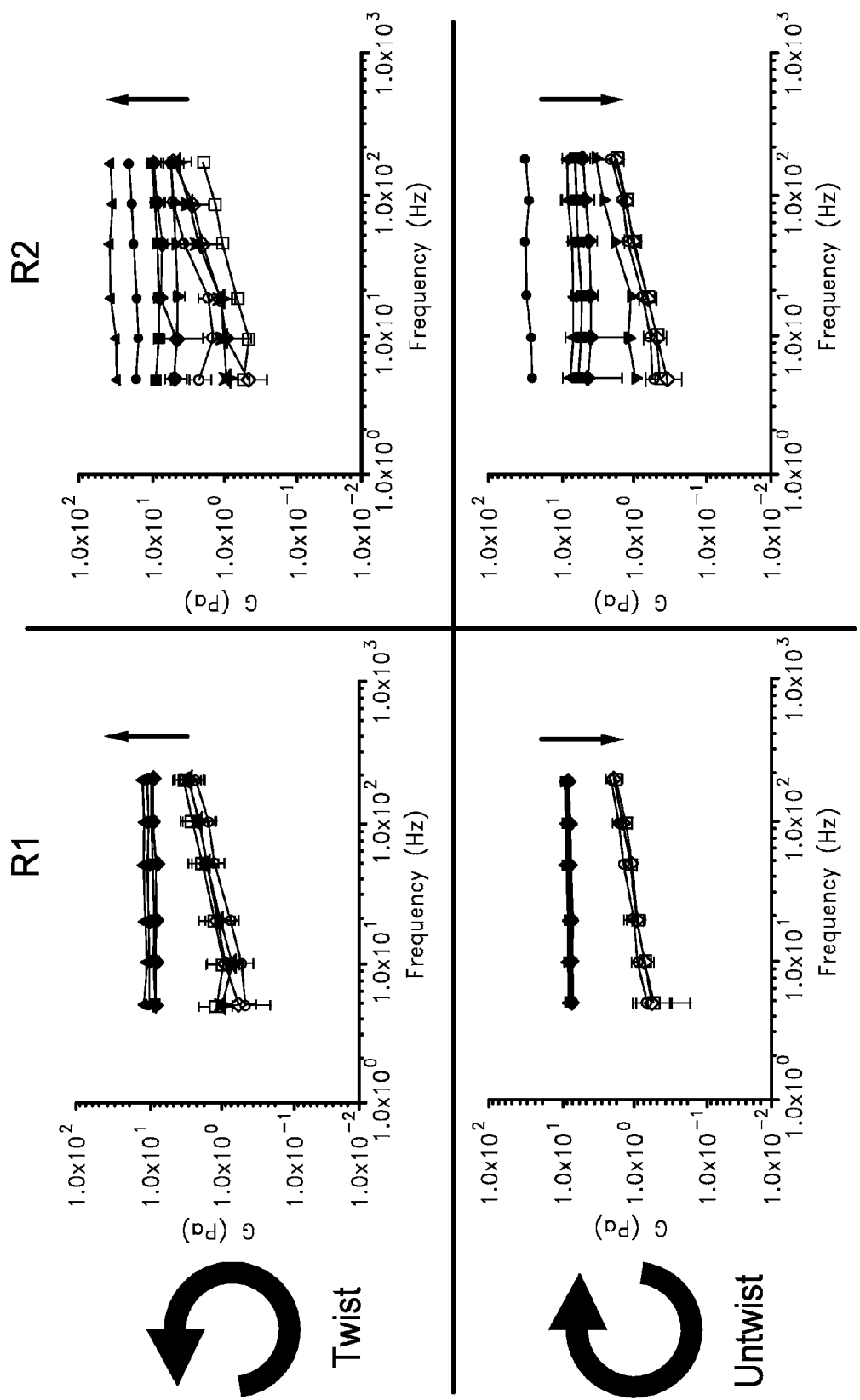
FIG. 19 illustrates G for a single bead as a post was rotated
Figure 20:
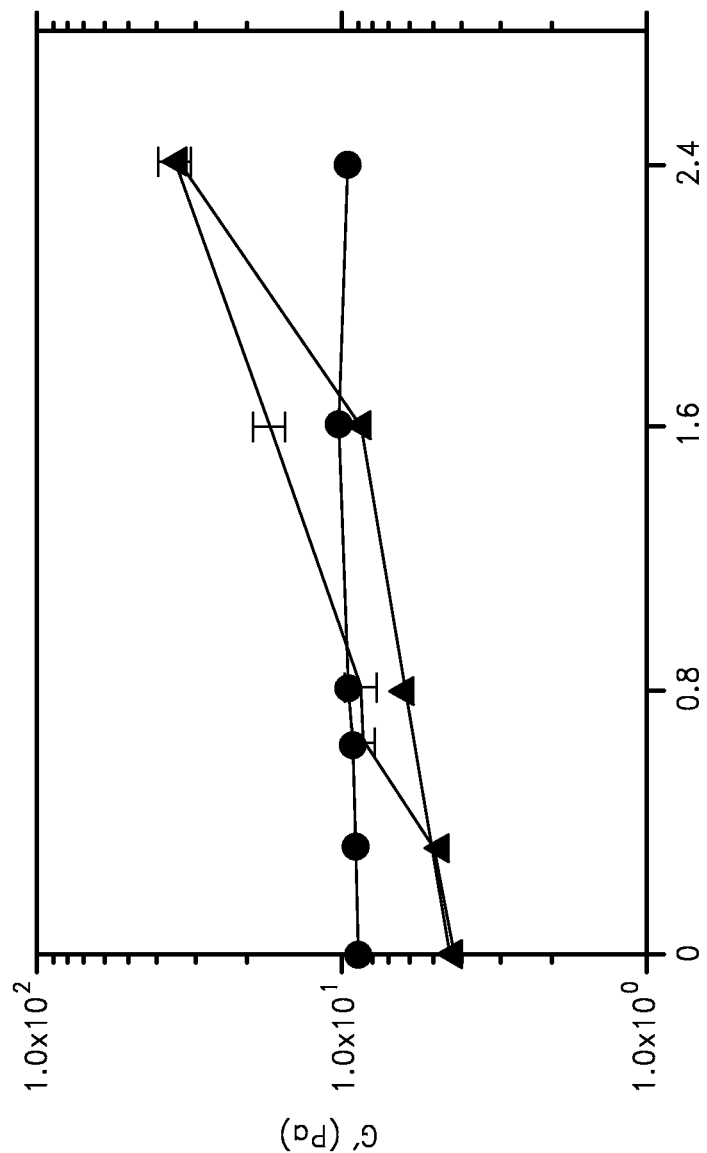
FIG. 20 illustrates stiffening and hysteresis after post rotation.

To directly measure the heterogeneity in stiffness within the apparatus, AMR was performed at 30 positions throughout a region of the gel as indicated in FIG. 18. At the center of each region, five neighboring microbeads were probed to determine the local distribution of G'. A pattern of stiffening consistent with our FEA model of strain and macroscopic measurement of strain stiffening was observed. Importantly, it was determined that the large endogenous variability in G' measured in unstressed gels could not account for the observed stiffening in our device, where the level of significance was relaxed to 0.15 for several regions. In further support of strain stiffening, G was measured for a single bead as the post was rotated by 0.0, 0.8, 1.6, and 2.4° in both region R1 and R2, as shown in FIG. 19. As shown in FIG. 19, AMR in R1, the region farthest from the post, reported no significant strain stiffening of the matrix even at 2.4° rotation of the post, a finding consistent with AFM studies of fibrin stiffness at low strain done by Winer et al, "Non-linear elasticity of extracellular matrices enables contractile cells to communicate local position and orientation," PLoS One 4: e6382, hereby incorporated by reference in its entirety. Non-linear elasticity of extracellular matrices enables contractile cells to communicate local position and orientation. PLoS One 4: e6382. As shown in FIG. 19 and FIG. 20, AMR in R2 reports both a 10-fold stiffening as well as hysteresis. Stiffening in R2 exhibited hysteresis where the material stiffened and softened along different paths as the post rotated. The material returned to its original stiffness as measured by AMR. No change in stiffness was observed in R1, the region farthest from the post. Each point in FIG. 19 is the mean G' of all measured frequencies.

AMR reports an increase in stiffness with increasing fibrin concentration in unstressed gels. This finding is consistent with the observed increase in mesh density and formation of fiber bundles by scanning fluorescence confocal microscopy. Surprisingly, examination of the 2.5 mg/ml fibrin mesh in R2 following rotation of the post by 2.4° suggests a translation of the mesh with no significant change in pore geometry for strained gels as shown in FIG. 3. Measured pore volume decreased with increasing fibrin concentration in unstressed gels ($p<0.05$), but not in R2 following rotation of the post. Thus local stretch can induce 10-fold stiffening without large deformations in pore geometry as assessed by diffraction limited light confocal microscopy.

Orbital Tracking Reveals Nanostructural Changes to Fibers

Figure 22:
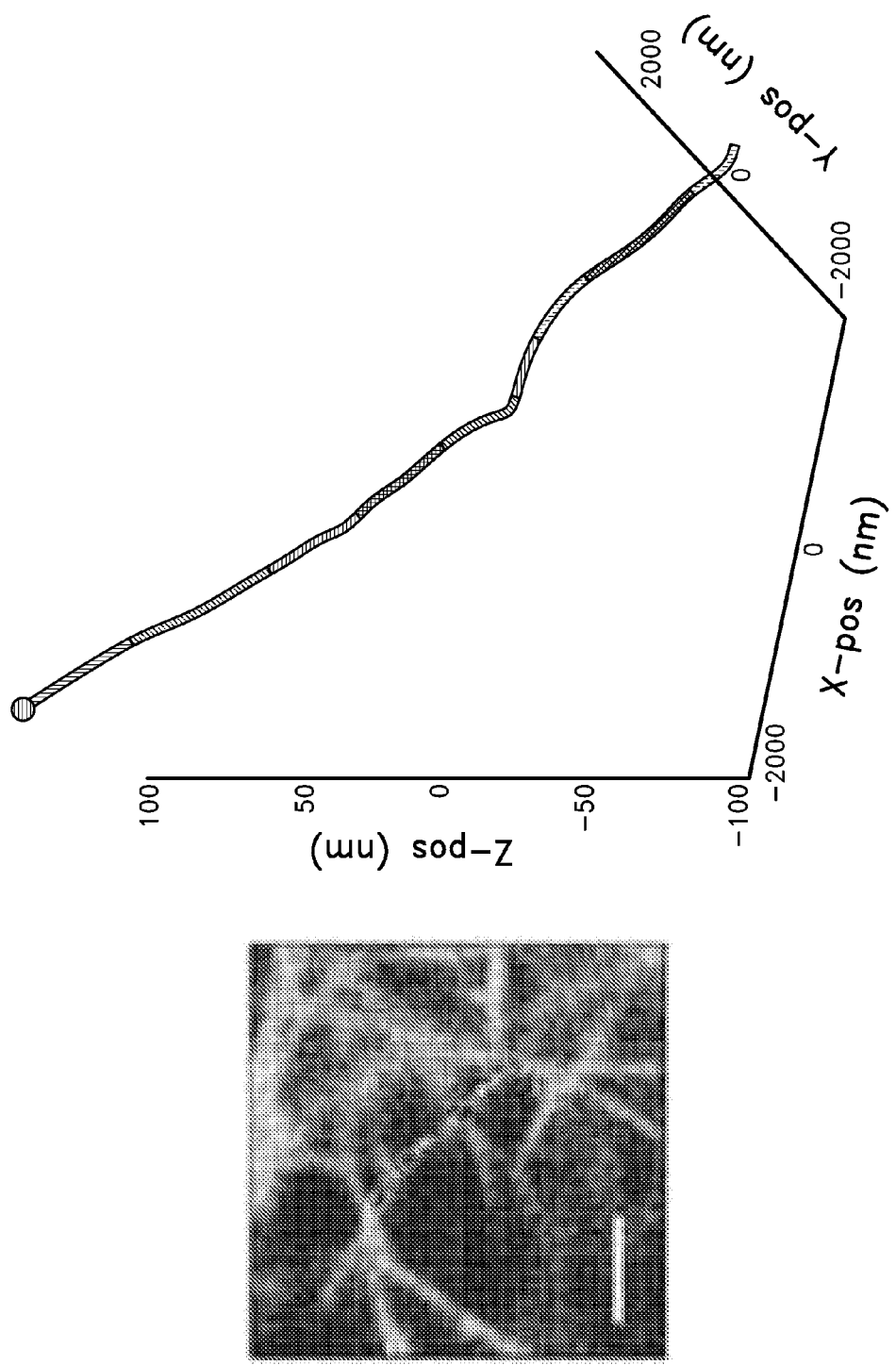
FIG. 22 illustrates straightened and elongated fibers.

To further investigate the mechanical basis of stiffening in R2, orbital tracking of fibers with and without applied stretch was implemented. In the absence of stretch, fibers appear buckled and coiled at the nanometer-scale, implying a slack state. Following rotation of the post by 2.4°, individual fibers transition from coiled, shown in FIG. 21, to straightened and elongated, shown in FIG. 22, consistent with the conformational change of a rope-like fiber under tension. In support of increased fiber tension with stretch, the maximum value of the MSD of the fiber midpoint after 200 seconds decreased with rotation of the post from approximately 60,000 $nm^2$ to 10,000 $nm^2$, as shown in FIG. 23. Moreover, fibers in this region were observed to recover to their original conformation as the post was unrotated, consistent with G' recovery measured by AMR.

Smooth Muscle Cell Culture in the Strain Gradient Device

Figure 24:
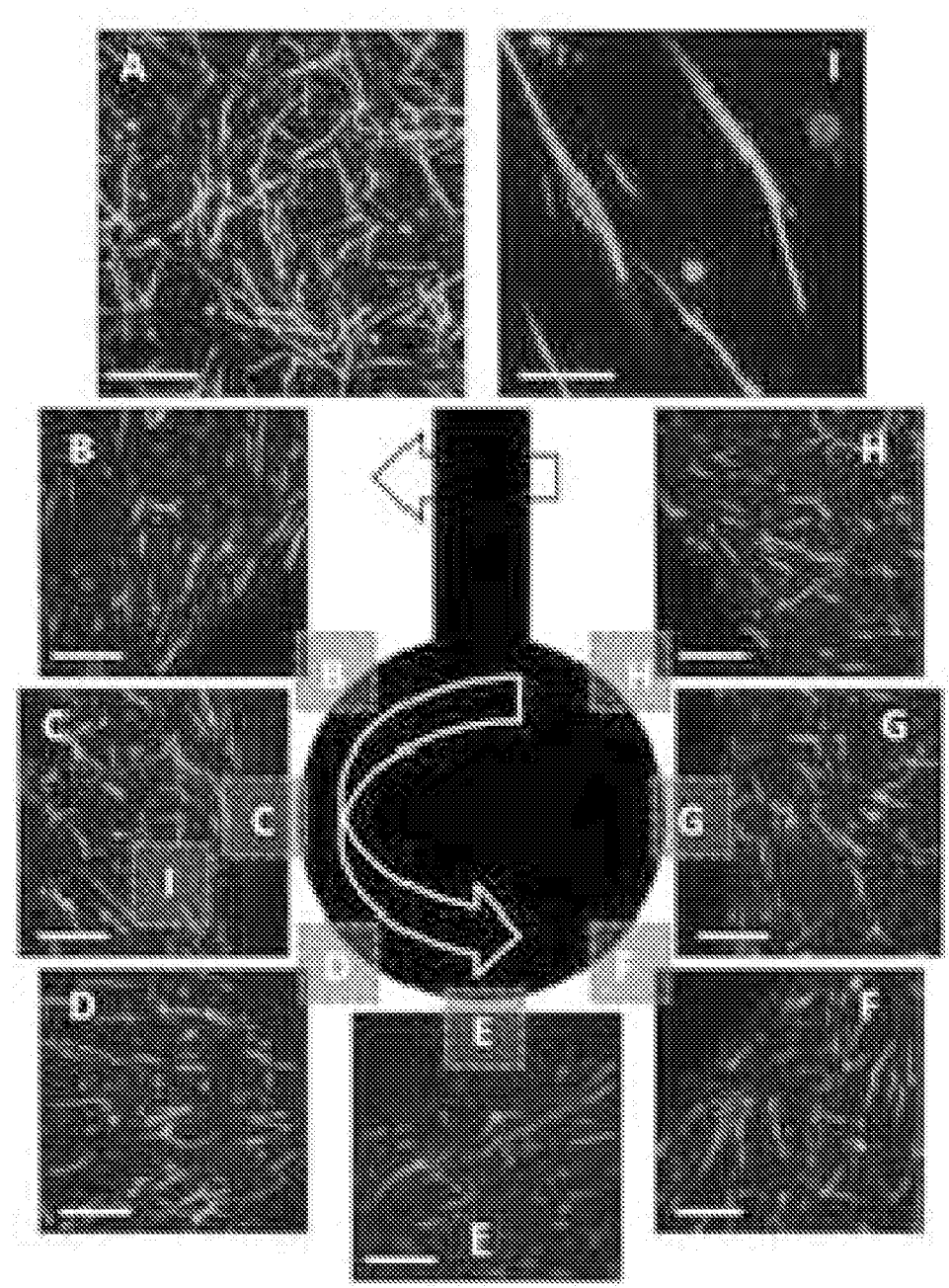
FIG. 24 illustrates the orientation of cells in different locations from a post.

Cells located far from the post in non-stiffened regions of the device were randomly oriented as shown in FIG. 24A. In contrast cells located near to the post appear partially aligned with the direction of post rotation as shown in FIG. 24B through FIG. 24I. In particular as shown in FIG. 24B through FIG. 24I, cells located less than approximately 200 μm from the post surface appear oriented with their long axis more tangent than normal to the surface of the post. AMR measurements of acellular fibrin gels indicate steep circumferential gradients within this region. Cells farther from the post exhibit a random orientation.

Discussion

Discussed above is a method for tuning the mechanical properties of naturally derived ECMs. Desirably for the method, there is a need to measure material properties at the same length scale as cells. Typically, material stiffness is measured macroscopically where the material can be assumed to act as a continuum. In order for the continuum assumption to apply, the characteristic length scale of underlying structural components must be much smaller than that of the physical model. In the above described system, fiber structure and architecture are near to the same scale as the cell itself. This compels us to probe the complex heterogeneous fibrous system by quantitative methods, such as AMR, to elucidate the role that local matrix stiffness plays in cellular physiology. Bulk measurements are in general insensitive to local micron scale heterogeneities. While the increase in stiffness with fibrin concentration was expected, the discrepancy between AMR and macrorheology highlights the requirement of measuring local micromechanics, particularly given the significant overlap in microrheological stiffness of 2.5, 5 and 10 mg/ml fibrin gels.

The spatial variability in stiffness revealed by AMR is expected under the assumption that local viscous and elastic moduli are dependent upon local mesh geometry, which is notably heterogeneous. In addition, the stiffness of an ECM is subject to temporal variability as cells dynamically alter their microenvironment through remodeling and the generation of cytoskeletal traction forces. While it is likely that cells actively remodel the local matrix through protease activity and the deposition of new ECM, it is also known that fibrin stiffness is modulated by cell-mediated mechanical stress as measured by AFM. This is because fibrin gels exhibit strain stiffening, which is typical of soft biological materials. It is important to note that methods of 3D traction force microscopy applied to naturally derived materials must include in situ real time measures of local stiffness since there will not be a simple relationship between bead displacement and cell forces when material properties are spatially and temporally variant. AMR's ability to track changes in local stiffness, in real time, make it an appropriate technique to complement 3D traction force microscopy.

As implemented above, AMR measures ECM stiffness in a local volume just larger than the bead. As a result, AMR has micron resolution allowing spatial mapping of stiffness around a cell as it dynamically interacts with its ECM. Here, the measured distribution of elastic moduli surrounding the cell implies it is exerting traction forces at its polar ends, which would cause local stretch-induced stiffening, consistent with observations of bead displacement for cells migrating in 3D. Therefore, in order to generate a complete model of the role of ECM stiffness in cell regulation, both the endogenous stiffness as well as local cell-mediated mechanical changes must be mapped using a nondestructive method such as AMR.

A ten-fold stiffening within a 2.5 mg/ml fibrin gel can be achieved as measured by AMR with no detectable change in pore geometry as measured by fluorescence confocal microscopy and image analysis of pore volume. The expected pore deformation or significant fiber alignment with the direction of stretch was not found, although straightening and elongation of fibers occurs at the nanoscale. These nanostructural and mechanical changes measured in fibrin are consistent with recent multiscale theories claiming that fibrin's resiliency arises from molecular level extension and alignment. A plausible explanation of the observed stiffening is that the strain induced by rotation of the post engaged covalent bonds within fibrin fibers thus stiffening the matrix as reported by AMR.

Differential AoSMCs alignment was observed within the apparatus suggesting cells were sensitive to the induced stiffness gradient. AoSMCs showed a strong circumferential alignment in the first few hundred microns from the post's surface. This is in agreement with FEA and AMR, which predicts circumferentially aligned principle strain, and reports strong circumferential gradients in stiffness respectively. Cells further from the post were randomly oriented, as were cells cultured in control dishes. The random orientation of cells in these low strain regions is consistent with AMR results, which indicate that the distribution of stiffness was unaltered with the application of strain. This preliminary result suggests that cells can respond to stiffness gradients developed in naturally derived ECMs by the application of non-uniform stretch. Therefore, the apparatus has the ability to measure and tune stiffness as well as the ability to image cell responses by diffraction limited fluorescence microscopy.

What is claimed is:

1. An apparatus for applying strain on an extracellular matrix (ECM) comprising:
   a base configured to securely hold a sample container comprising an ECM;
   a post configured to contact the ECM; and
   a means for imparting a rotational strain on the ECM comprising a threaded screw, a spring plunger assembly and a lever arm, configured to rotate the post relative to the sample container.

2. The apparatus of claim 1 wherein the means for imparting rotational strain further comprises a notch on the sample container and a lever configured to rotate the sample container relative to the post.

3. The apparatus of claim 1 wherein the means for imparting rotational strain further comprises a motor configured to rotate the sample container or the post.

4. The apparatus of claim 1 wherein a force meter is attached to the post or sample container.

5. The apparatus of claim 1 wherein the sample container is a petri dish or a cell culture dish.

6. The apparatus of claim 1 wherein the rotational strain is non-uniform throughout the ECM.

7. The apparatus of claim 1 wherein the rotational strain can be applied in both a clockwise and a counterclockwise direction.

8. An apparatus for providing a strain gradient to an extracellular matrix (ECM) comprising:
   at least one sample area configured to hold an ECM;
   a post configured to contact the ECM;
   a threaded screw;
   a spring plunger assembly; and
   a lever arm with a first end attached to the post and a second end positioned between the threaded screw and the spring plunger assembly.

9. A method for applying strain on an extracellular matrix (ECM) comprising:
   providing an ECM within a sample container;
   contacting a post with the ECM; and
   rotating the post relative to the sample container using a threaded screw, a spring plunger assembly and a lever arm to create rotational strain on the ECM.

10. The method of claim 9 wherein the sample container further comprises cells.

11. The method of claim 9 wherein prior to rotating the post, the ECM is incubated with the post for a time sufficient to promote adhesion of the ECM to the post.

12. The method of claim 9 wherein the surface area of the post in contact with the ECM is smaller than the surface area of the sample container.

13. The method of claim 9 wherein the ECM has a higher stiffness nearer to the post as compared to the ECM farther from the post.

14. The method of claim 9 wherein the ECM does not increase in stiffness.

15. The method of claim 9 wherein the ECM has a limited change in pore geometry.

16. The method of claim 9 wherein fibers within the ECM has tension applied.

17. The method of claim 9 wherein the rotating of the post causes non-uniform strain throughout the ECM.

18. The method of claim 9 wherein the post is rotated in both a clockwise and a counterclockwise direction.

19. The method of claim 9 wherein both the post and the sample container are rotated.

20. The apparatus of claim 1 comprising a coupling configured to connect to a microscope.

\* \* \* \* \*

UNITED STATES PATENT AND TRADEMARK OFFICE
CERTIFICATE OF CORRECTION

PATENT NO. : 8,844,369 B2
APPLICATION NO. : 13/457342
DATED : September 30, 2014
INVENTOR(S) : Elliot L. Botvinick It is certified that error appears in the above-identified patent and that said Letters Patent is hereby corrected as shown below:

In the Specification

In column 12 line 51 (approx.), Change "$x_j(t)$" to --$x_f(t)$--.

In column 13 line 22 (approx.), Change "'$\alpha$'" to --'$a$'--.

In column 16 line 61, Change "24l." to --24I.--.

In column 16 line 62, Change "24l," to --24I,--.

Signed and Sealed this
Seventh Day of April, 2015

Michelle K. Lee
*Director of the United States Patent and Trademark Office*